(12) United States Patent
Edwards

(10) Patent No.: US 11,883,260 B2
(45) Date of Patent: Jan. 30, 2024

(54) DELIVERY APPARATUS, SYSTEM AND ASSOCIATED METHODS

(71) Applicant: Automed Patent Holdco, LLC, Loveland, CO (US)

(72) Inventor: David Royce Edwards, New Lambton (AU)

(73) Assignee: Automed Patent Holdco, LLC, Loveland, CO (US)

( * ) Notice: Subject to any disclaimer, the term of this patent is extended or adjusted under 35 U.S.C. 154(b) by 677 days.

(21) Appl. No.: 15/538,213

(22) PCT Filed: Dec. 22, 2015

(86) PCT No.: PCT/AU2015/050832
§ 371 (c)(1),
(2) Date: Jun. 21, 2017

(87) PCT Pub. No.: WO2016/101031
PCT Pub. Date: Jun. 30, 2016

(65) Prior Publication Data
US 2017/0340424 A1     Nov. 30, 2017

(30) Foreign Application Priority Data
Dec. 23, 2014   (AU) ................. 2014905258

(51) Int. Cl.
*A61D 7/00*     (2006.01)
*A61M 5/20*     (2006.01)
*G16H 20/17*    (2018.01)

(52) U.S. Cl.
CPC ............. *A61D 7/00* (2013.01); *A61M 5/20* (2013.01); *A61M 5/204* (2013.01); *A61M 2205/50* (2013.01); *G16H 20/17* (2018.01)

(58) Field of Classification Search
CPC ........... A61D 7/00; A61M 5/20; A61M 5/204; A61M 2205/50; A61M 5/48; A61M 2205/3331; A61M 5/16854; G06F 19/3468
See application file for complete search history.

(56) References Cited

U.S. PATENT DOCUMENTS 3,941,130 A   3/1976  Tibbs
4,073,321 A   2/1978  Moskowitz
(Continued)

FOREIGN PATENT DOCUMENTS

CA   2267812 A1   10/2000
EP   2656865      10/2013
(Continued)

OTHER PUBLICATIONS

International-Type Search Report of AU2014905258 dated Nov. 26, 2015, 11 pages.
(Continued)

*Primary Examiner* — Lauren P Farrar

(57) ABSTRACT

An apparatus, a system and methods are disclosed in relation to the configuration and compatibility of a removable delivery section of the apparatus, and delivering a substance via the apparatus to an animal. In an aspect, a hand held apparatus for delivering a substance to an animal includes a removable delivery section including a delivery arrangement adapted to deliver the substance to the animal; and a drive section including a drive arrangement adapted to actuate the delivery arrangement in a coupled condition in which the removable delivery section is coupled to the drive section. The delivery section includes an electronic device adapted to communicate with a control system associated with at least the drive section in the coupled condition, the electronic device being configurable so to be readable by the
(Continued)

control system such that the control system is able to identify and operate the removable delivery section.

18 Claims, 19 Drawing Sheets

(56) References Cited

U.S. PATENT DOCUMENTS

| | | |
|---|---|---|
| 4,103,684 A | 8/1978 | Ismach |
| 4,106,770 A | 8/1978 | Gray |
| 4,261,358 A | 4/1981 | Vargas et al. |
| 4,275,729 A | 6/1981 | Silver et al. |
| 4,316,463 A | 2/1982 | Schmitz et al. |
| 4,435,173 A * | 3/1984 | Siposs .............. A61M 5/1456 128/DIG. 1 |
| 4,475,905 A | 10/1984 | Himmelstrup |
| 4,498,904 A | 2/1985 | Turner et al. |
| 4,547,189 A | 10/1985 | Moore, Jr. |
| 4,592,742 A | 6/1986 | Landau |
| 4,664,653 A | 5/1987 | Sagstetter et al. |
| 4,710,162 A | 12/1987 | Johnson |
| 4,735,611 A | 4/1988 | Anderson et al. |
| 4,738,660 A | 4/1988 | Lucas |
| 4,852,768 A | 8/1989 | Bartsch |
| 4,858,607 A | 8/1989 | Jordan et al. |
| 4,865,591 A | 9/1989 | Sams |
| 4,902,279 A | 2/1990 | Schmidtz et al. |
| 4,955,868 A | 9/1990 | Klein |
| 4,988,339 A | 1/1991 | Vadher |
| 4,994,034 A | 2/1991 | Botich et al. |
| 5,011,476 A | 4/1991 | Foster |
| 5,026,349 A | 6/1991 | Schmitz et al. |
| 5,127,906 A | 7/1992 | Landry, Jr. et al. |
| 5,151,088 A | 9/1992 | Allison et al. |
| 5,163,908 A | 11/1992 | Lambert |
| 5,176,643 A | 1/1993 | Kramer et al. |
| 5,190,526 A | 3/1993 | Murray et al. |
| 5,201,720 A | 4/1993 | Borgia et al. |
| 5,226,896 A | 7/1993 | Harris |
| 5,232,459 A | 8/1993 | Hjertman |
| 5,267,963 A | 12/1993 | Bachynsky |
| 5,271,744 A | 12/1993 | Kramer et al. |
| 5,298,024 A | 3/1994 | Richmond |
| 5,300,041 A | 4/1994 | Haber et al. |
| 5,304,152 A | 4/1994 | Sams |
| 5,320,609 A | 6/1994 | Haber et al. |
| 5,322,511 A | 6/1994 | Armbruster et al. |
| 5,346,480 A | 9/1994 | Hess et al. |
| 5,358,489 A | 10/1994 | Wyrick |
| 5,364,362 A | 11/1994 | Schulz |
| 5,391,157 A | 2/1995 | Harris et al. |
| 5,411,487 A | 5/1995 | Castagna |
| 5,451,210 A | 9/1995 | Kramer et al. |
| 5,514,097 A | 5/1996 | Knauer |
| 5,545,147 A | 8/1996 | Harris |
| 5,560,317 A | 10/1996 | Bunyan et al. |
| 5,562,626 A | 10/1996 | Sanpietro |
| 5,573,513 A | 11/1996 | Wozencroft |
| 5,599,309 A | 2/1997 | Marshall et al. |
| 5,620,421 A | 4/1997 | Schmitz |
| 5,626,566 A | 5/1997 | Petersen et al. |
| 5,695,472 A | 12/1997 | Wyrick |
| 5,713,871 A | 2/1998 | Stock |
| 5,722,956 A | 3/1998 | Sims et al. |
| 5,769,822 A | 6/1998 | McGary et al. |
| 5,776,107 A | 7/1998 | Cherif-Cheikh |
| 5,779,677 A | 7/1998 | Frezza |
| 5,792,117 A | 8/1998 | Brown |
| 5,800,403 A | 9/1998 | Pressly et al. |
| 5,833,669 A | 11/1998 | Wyrick |
| 5,882,342 A | 3/1999 | Cooper et al. |
| 5,911,703 A | 6/1999 | Slate et al. |
| 5,921,959 A | 7/1999 | McGary et al. |
| 5,984,900 A | 11/1999 | Mikkelsen |
| 5,984,906 A | 11/1999 | Bonnichsen et al. |
| 5,997,500 A | 12/1999 | Cook et al. |
| 6,015,438 A | 1/2000 | Shaw |
| 6,056,716 A | 5/2000 | D'Antonio et al. |
| 6,068,615 A | 5/2000 | Brown et al. |
| 6,077,247 A | 6/2000 | Marshall et al. |
| 6,083,199 A | 7/2000 | Thorley et al. |
| 6,086,567 A | 7/2000 | Kirchhofer et al. |
| 6,099,504 A | 8/2000 | Gross et al. |
| 6,102,896 A | 8/2000 | Roser |
| 6,110,147 A | 8/2000 | Perouse |
| 6,171,285 B1 | 1/2001 | Johnson |
| 6,179,812 B1 | 1/2001 | Botich et al. |
| 6,203,530 B1 | 3/2001 | Stewart |
| 6,221,044 B1 | 4/2001 | Greco |
| 6,270,479 B1 | 8/2001 | Bergens et al. |
| 6,277,101 B1 | 8/2001 | Kirchhofer et al. |
| 6,312,412 B1 | 11/2001 | Saied et al. |
| 6,319,234 B1 | 11/2001 | Restelli et al. |
| 6,368,303 B1 | 4/2002 | Caizza |
| 6,387,078 B1 | 5/2002 | Gillespie, III |
| 6,391,003 B1 | 5/2002 | Lesch, Jr. |
| 6,398,762 B1 | 6/2002 | Vetter et al. |
| 6,413,237 B1 | 7/2002 | Caizza et al. |
| 6,428,528 B2 | 8/2002 | Sadowski et al. |
| 6,432,087 B1 | 8/2002 | Hoeck et al. |
| 6,461,333 B1 | 10/2002 | Frezza |
| 6,482,176 B1 | 11/2002 | Wich |
| 6,482,185 B1 | 11/2002 | Hartmann |
| 6,511,460 B1 | 1/2003 | Arnissolle |
| 6,530,903 B2 | 3/2003 | Wang et al. |
| 6,547,764 B2 | 4/2003 | Larsen et al. |
| 6,558,352 B1 | 5/2003 | Hogan |
| 6,558,357 B1 | 5/2003 | Hoeck |
| 6,569,123 B2 | 5/2003 | Alchas et al. |
| 6,569,143 B2 | 5/2003 | Alchas et al. |
| 6,589,210 B1 | 7/2003 | Rolfe |
| 6,599,272 B1 | 7/2003 | Hjertman et al. |
| 6,605,058 B1 | 8/2003 | Wich |
| 6,607,508 B2 | 8/2003 | Knauer |
| 6,610,042 B2 | 8/2003 | Leon et al. |
| 6,638,255 B1 | 10/2003 | Weber |
| 6,648,858 B2 | 11/2003 | Asbaghi |
| 6,656,163 B1 | 12/2003 | Marshall et al. |
| 6,656,164 B1 | 12/2003 | Smith |
| 6,689,118 B2 | 2/2004 | Alchas et al. |
| 6,692,463 B1 | 2/2004 | Marteau et al. |
| 6,692,469 B1 | 2/2004 | Weekes et al. |
| 6,699,220 B2 | 3/2004 | Rolfe |
| 6,726,661 B2 | 4/2004 | Munk et al. |
| 6,776,776 B2 | 8/2004 | Alchas et al. |
| 6,805,686 B1 | 10/2004 | Fathallah et al. |
| 6,808,507 B2 | 10/2004 | Roser |
| 6,817,989 B2 | 11/2004 | Svendsen et al. |
| 6,843,781 B2 | 1/2005 | Alchas et al. |
| 6,890,319 B1 | 5/2005 | Crocker |
| 6,976,976 B2 | 12/2005 | Doyle |
| 6,979,316 B1 | 12/2005 | Rubin et al. |
| 7,011,649 B2 | 3/2006 | Serna et al. |
| 7,056,307 B2 | 6/2006 | Smith et al. |
| 7,097,634 B2 | 8/2006 | Gilbert |
| 7,104,969 B2 | 9/2006 | Plessis |
| 7,112,187 B2 | 9/2006 | Karlsson |
| 7,229,432 B2 | 6/2007 | Marshall et al. |
| 7,241,278 B2 | 7/2007 | Møller |
| 7,247,151 B2 | 7/2007 | Slawson |
| 7,252,651 B2 | 8/2007 | Haider et al. |
| 7,500,963 B2 | 3/2009 | Westbye et al. |
| 7,500,967 B2 | 3/2009 | Thorley et al. |
| 7,597,685 B2 | 10/2009 | Olson |
| 7,615,234 B2 | 11/2009 | Potter et al. |
| 7,621,891 B2 | 11/2009 | Wyrick |
| 7,637,891 B2 | 12/2009 | Wall |
| 7,645,265 B2 | 1/2010 | Stamp |
| 7,670,314 B2 | 3/2010 | Wall et al. |
| 7,674,246 B2 | 3/2010 | Gillespie et al. |
| 7,727,201 B2 | 6/2010 | Kirchhofer |
| 7,785,292 B2 | 8/2010 | Harrison |
| RE41,956 E | 11/2010 | Klitgaard et al. |
| 7,896,850 B2 | 3/2011 | Kronestedt et al. |

(56) References Cited

U.S. PATENT DOCUMENTS

| | | |
|---|---|---|
| 7,905,352 B2 | 3/2011 | Wyrick |
| 7,918,824 B2 | 4/2011 | Bishop et al. |
| 7,935,087 B2 | 5/2011 | Judd et al. |
| 7,976,509 B2 | 7/2011 | Moser et al. |
| 7,976,510 B2 | 7/2011 | Janish et al. |
| 7,981,088 B2 | 7/2011 | Westbye et al. |
| 7,988,675 B2 | 8/2011 | Gillespie, III et al. |
| 8,002,745 B2 | 8/2011 | Kaal et al. |
| 8,012,131 B2 | 9/2011 | Moser et al. |
| 8,021,333 B2 | 9/2011 | Kaal et al. |
| 8,021,335 B2 | 9/2011 | Lesch, Jr. |
| 8,052,645 B2 | 11/2011 | Slate et al. |
| 8,052,655 B2 | 11/2011 | Møller et al. |
| 8,114,050 B2 | 2/2012 | Kaal et al. |
| 8,172,813 B2 | 5/2012 | Janish |
| 8,177,749 B2 | 5/2012 | Slate et al. |
| 8,187,226 B2 | 5/2012 | Stamp et al. |
| 8,197,450 B2 | 6/2012 | Glejbol et al. |
| 8,267,890 B2 | 9/2012 | Alchas et al. |
| 8,298,194 B2 | 10/2012 | Møller |
| 8,308,687 B2 | 11/2012 | Carrel et al. |
| 8,343,103 B2 | 1/2013 | Moser |
| 8,353,878 B2 | 1/2013 | Moller et al. |
| 8,357,120 B2 | 1/2013 | Moller et al. |
| 8,361,036 B2 | 1/2013 | Møller et al. |
| 8,366,682 B2 | 2/2013 | Wyrick |
| 8,376,993 B2 | 2/2013 | Cox et al. |
| 8,409,141 B2 | 4/2013 | Johansen et al. |
| 8,608,708 B2 | 12/2013 | Cowe |
| 8,636,704 B2 | 1/2014 | Shang et al. |
| 8,734,403 B2 | 5/2014 | Hirschel et al. |
| 8,784,381 B2 | 7/2014 | Watanabe et al. |
| 8,900,197 B2 | 12/2014 | Crow |
| 8,905,970 B2 | 12/2014 | Bates et al. |
| 8,913,123 B2 | 12/2014 | Miller |
| 8,915,886 B2 | 12/2014 | Cowe |
| 8,920,374 B2 | 12/2014 | Bokelman et al. |
| 8,932,254 B2 | 1/2015 | Eaton |
| 8,932,266 B2 | 1/2015 | Wozencroft |
| 8,945,063 B2 | 2/2015 | Wotton et al. |
| 8,992,484 B2 | 3/2015 | Radmer et al. |
| 8,998,855 B2 | 4/2015 | Hudson et al. |
| 9,011,386 B2 | 4/2015 | Kronestedt et al. |
| 9,017,293 B2 | 4/2015 | Edhouse et al. |
| 9,022,989 B2 | 5/2015 | Bicknell et al. |
| 9,044,378 B2 | 6/2015 | Verespej et al. |
| 9,044,553 B2 | 6/2015 | James et al. |
| 9,101,722 B2 | 8/2015 | Moller |
| 9,108,006 B2 | 8/2015 | Jensen et al. |
| 9,114,212 B2 | 8/2015 | Enggaard et al. |
| 9,114,216 B2 | 8/2015 | Sutkin et al. |
| 9,138,542 B2 | 9/2015 | Smith |
| 9,144,648 B2 | 9/2015 | Lesch, Jr. et al. |
| 9,155,844 B2 | 10/2015 | Brereton et al. |
| 9,192,727 B2 | 11/2015 | Møller et al. |
| 9,199,039 B2 | 12/2015 | Moser et al. |
| 9,199,041 B2 | 12/2015 | Edginton |
| 9,216,256 B2 | 12/2015 | Olson et al. |
| 9,233,213 B2 | 1/2016 | Olson et al. |
| 9,248,245 B2 | 2/2016 | Ekman et al. |
| 9,333,309 B2 | 5/2016 | Sadowski et al. |
| 9,339,609 B2 | 5/2016 | Ekman et al. |
| 9,352,089 B2 | 5/2016 | Hourmand et al. |
| 9,381,308 B2 | 7/2016 | Hemmann et al. |
| 9,402,954 B1 | 8/2016 | Slevin |
| 9,408,973 B2 | 8/2016 | Shang et al. |
| 9,446,204 B2 | 9/2016 | Teucher et al. |
| 9,457,147 B2 | 10/2016 | Green |
| 9,457,149 B2 | 10/2016 | Kemp et al. |
| 9,457,153 B2 | 10/2016 | Marano, Jr. et al. |
| 9,457,154 B2 | 10/2016 | Moller et al. |
| 9,463,282 B2 | 10/2016 | Barrow-Williams et al. |
| 9,474,866 B2 | 10/2016 | Hourmand et al. |
| 9,486,581 B2 | 11/2016 | Lovell et al. |
| 9,486,583 B2 | 11/2016 | Lannan et al. |
| 9,517,311 B2 | 12/2016 | Saiki |
| 9,539,392 B2 | 1/2017 | Jennings et al. |
| 9,545,481 B1 | 1/2017 | Rafaat |
| 9,579,468 B2 | 2/2017 | Schoonmaker et al. |
| 9,592,350 B2 | 3/2017 | Roberts et al. |
| 9,616,178 B2 | 4/2017 | Butler et al. |
| 9,656,025 B2 | 5/2017 | Boström et al. |
| 9,724,472 B2 | 8/2017 | Hourmand et al. |
| 9,724,479 B2 | 8/2017 | Sutkin et al. |
| 9,744,297 B2 | 8/2017 | Cabiri et al. |
| 9,750,885 B2 | 9/2017 | Weaver et al. |
| 9,757,520 B2 | 9/2017 | Corrigan |
| 9,757,523 B2 | 9/2017 | Macdonald et al. |
| 9,764,089 B2 | 9/2017 | Alexandersson |
| 9,814,836 B2 | 11/2017 | Cowe |
| 9,821,118 B2 | 11/2017 | Adlon et al. |
| 9,827,373 B2 | 11/2017 | Roervig et al. |
| 9,901,680 B2 | 2/2018 | Roervig et al. |
| 9,901,681 B2 | 2/2018 | Sweeney et al. |
| 9,925,333 B2 | 3/2018 | Hooven et al. |
| 9,931,471 B2 | 4/2018 | Ekman et al. |
| 9,943,649 B2 | 4/2018 | Shang et al. |
| 9,950,125 B2 | 4/2018 | Wotton et al. |
| 9,956,344 B2 | 5/2018 | Cleathero |
| 9,974,904 B2 | 5/2018 | Burk et al. |
| 9,974,905 B2 | 5/2018 | Butler et al. |
| 10,052,436 B2 | 8/2018 | Högdahl |
| 10,052,441 B2 | 8/2018 | Searle et al. |
| 10,076,356 B2 | 9/2018 | Hadvary et al. |
| 10,092,708 B2 | 10/2018 | Thorley et al. |
| 10,117,996 B2 | 11/2018 | Stefansen |
| 10,130,768 B2 | 11/2018 | Dungar et al. |
| 10,143,625 B2 | 12/2018 | Li et al. |
| 10,159,796 B2 | 12/2018 | Schiff et al. |
| 10,179,207 B2 | 1/2019 | Haupt |
| 10,195,351 B2 | 2/2019 | Allerdings et al. |
| 10,226,585 B2 | 3/2019 | Franklin et al. |
| 10,259,835 B2 | 4/2019 | Siddiqui-Jain et al. |
| 10,265,471 B2 | 4/2019 | Kapas et al. |
| 10,265,476 B2 | 4/2019 | Laiosa et al. |
| 10,265,478 B2 | 4/2019 | Kouyoumjian et al. |
| 10,269,266 B2 | 4/2019 | Rios et al. |
| 10,279,116 B2 | 5/2019 | Plumptre et al. |
| 10,300,201 B2 | 5/2019 | Lumme et al. |
| 10,300,206 B2 | 5/2019 | Bergens et al. |
| 10,376,641 B2 | 8/2019 | Hirschel et al. |
| 10,376,692 B2 | 8/2019 | Mathiesen et al. |
| 10,391,252 B2 | 8/2019 | Haupt |
| 10,391,259 B2 | 8/2019 | Tran et al. |
| 10,398,842 B2 | 9/2019 | Niven et al. |
| 10,406,291 B2 | 9/2019 | Hansen et al. |
| 10,413,667 B2 | 9/2019 | Henderson et al. |
| 10,413,680 B2 | 9/2019 | Shimizu et al. |
| 10,512,733 B2 | 12/2019 | Roberts et al. |
| RE47,903 E | 3/2020 | Hourmand et al. |
| 10,588,729 B2 | 3/2020 | Moons et al. |
| 10,625,026 B2 | 4/2020 | Creaturo |
| 10,653,830 B2 | 5/2020 | Limaye |
| 10,661,014 B2 | 5/2020 | Sarkinen et al. |
| 10,675,415 B2 | 6/2020 | Takabatake et al. |
| 10,737,030 B2 | 8/2020 | Molson et al. |
| 10,744,269 B2 | 8/2020 | Veasey et al. |
| 10,751,483 B2 | 8/2020 | Hatch et al. |
| 10,888,662 B2 | 1/2021 | Cave |
| 10,898,648 B2 | 1/2021 | Taylor et al. |
| 10,912,892 B2 | 2/2021 | Edwards |
| 10,960,130 B2 | 3/2021 | Schiff et al. |
| 10,967,127 B2 | 4/2021 | Murakami et al. |
| 10,995,125 B2 | 5/2021 | Flinspach et al. |
| RE48,593 E | 6/2021 | Hourmand et al. |
| 11,027,056 B2 | 6/2021 | Mcmahon |
| 11,065,386 B2 | 7/2021 | Atterbury et al. |
| 11,090,441 B2 | 8/2021 | Tran et al. |
| 11,090,445 B2 | 8/2021 | Diaz et al. |
| 11,097,053 B2 | 8/2021 | Veyrent et al. |
| 11,167,086 B2 | 11/2021 | Cabiri et al. |
| 11,278,677 B2 | 3/2022 | Erbstein et al. |
| 11,318,252 B2 | 5/2022 | Zhang |
| 11,357,925 B2 | 6/2022 | Dugand et al. |

(56) References Cited

U.S. PATENT DOCUMENTS

| | | |
|---|---|---|
| 11,376,364 B2 | 7/2022 | Dobson et al. |
| 11,376,373 B2 | 7/2022 | Perot et al. |
| 11,419,991 B2 | 8/2022 | Diaz et al. |
| 11,433,186 B2 | 9/2022 | Ulla |
| 11,439,762 B2 | 9/2022 | Toporek et al. |
| 11,565,051 B2 | 1/2023 | Helmer |
| 11,571,518 B2 | 2/2023 | Flather et al. |
| 11,642,462 B2 | 5/2023 | Stamp |
| 11,660,397 B2 | 5/2023 | Moeller |
| 11,672,904 B2 | 6/2023 | Cabiri et al. |
| 2002/0004652 A1 | 1/2002 | Asbaghi |
| 2002/0107501 A1 | 8/2002 | Smith et al. |
| 2002/0161337 A1 | 10/2002 | Shaw et al. |
| 2003/0023205 A1 | 1/2003 | Botich et al. |
| 2003/0109833 A1 | 6/2003 | Sharpe |
| 2003/0114799 A1 | 6/2003 | Cheikh |
| 2004/0068158 A1 | 4/2004 | Bennett |
| 2004/0133161 A1* | 7/2004 | Trocki ............... A61M 39/10 604/131 |
| 2004/0143224 A1 | 7/2004 | Field et al. |
| 2004/0147875 A1 | 7/2004 | Wallace et al. |
| 2005/0090782 A1 | 4/2005 | Marshall et al. |
| 2005/0171476 A1 | 8/2005 | Judson et al. |
| 2005/0222539 A1 | 10/2005 | Gonzales et al. |
| 2006/0069350 A1 | 3/2006 | Buenger et al. |
| 2006/0069354 A1 | 3/2006 | Buenger et al. |
| 2006/0129122 A1 | 6/2006 | Wyrick |
| 2007/0017533 A1 | 1/2007 | Wyrick |
| 2007/0021720 A1 | 1/2007 | Guillermo |
| 2007/0203247 A1 | 8/2007 | Phillips et al. |
| 2007/0265568 A1 | 11/2007 | Tsals et al. |
| 2008/0071218 A1* | 3/2008 | D'Antonio ............ A61M 5/30 604/152 |
| 2008/0147006 A1 | 6/2008 | Brunnberg et al. |
| 2008/0208142 A1 | 8/2008 | Moller |
| 2008/0228147 A1 | 9/2008 | David-Hegerich et al. |
| 2009/0005737 A1 | 1/2009 | Chun |
| 2009/0204076 A1 | 8/2009 | Liversidge |
| 2009/0240210 A1 | 9/2009 | Walton et al. |
| 2010/0016796 A1 | 1/2010 | Derichs |
| 2010/0049140 A1 | 2/2010 | Marsh et al. |
| 2010/0256554 A1 | 10/2010 | Discher, Jr. et al. |
| 2011/0224613 A1 | 9/2011 | D Antonio et al. |
| 2011/0226646 A1 | 9/2011 | Wyrick |
| 2012/0179132 A1* | 7/2012 | Valk ................. A61M 5/1452 604/500 |
| 2012/0233834 A1 | 9/2012 | Szechinski et al. |
| 2012/0296276 A1 | 11/2012 | Nicholls et al. |
| 2012/0316435 A1 | 12/2012 | Burg et al. |
| 2013/0211337 A1 | 8/2013 | Hofmann |
| 2013/0274677 A1 | 10/2013 | Ekman et al. |
| 2013/0331796 A1 | 12/2013 | Wozencroft |
| 2014/0135705 A1 | 5/2014 | Hourmand et al. |
| 2014/0248605 A1 | 9/2014 | Loneragan et al. |
| 2014/0276583 A1* | 9/2014 | Chen ............... A61M 5/31546 604/207 |
| 2015/0001285 A1* | 1/2015 | Halbert ............... G16H 20/17 235/375 |
| 2015/0202373 A1 | 7/2015 | Creaturo |
| 2015/0209515 A1* | 7/2015 | Houde ............... A61M 5/19 600/432 |
| 2015/0209519 A1 | 7/2015 | Mernøe |
| 2017/0000949 A1 | 1/2017 | Franklin et al. |
| 2017/0072130 A1 | 3/2017 | Mcmahon |
| 2017/0348486 A1 | 12/2017 | Andersen et al. |
| 2018/0154082 A1 | 6/2018 | Yoh et al. |
| 2019/0143041 A1 | 5/2019 | Gould |
| 2019/0175839 A1 | 6/2019 | Kwolek et al. |
| 2020/0188599 A1 | 6/2020 | Mandaroux et al. |
| 2021/0236623 A1 | 8/2021 | Georges et al. |
| 2021/0338402 A1 | 11/2021 | Magyar et al. |

FOREIGN PATENT DOCUMENTS

| | | |
|---|---|---|
| WO | 2008091838 | 7/2008 |
| WO | 2013110624 | 8/2013 |
| WO | 2014090252 | 6/2014 |
| WO | 2014107766 | 7/2014 |
| WO | 2014143815 | 9/2014 |

OTHER PUBLICATIONS

Notification of Transmittal of the International Search Report and the Written Opinion of the International Searching Authority, or the Declaration of PCT/AU2015/050832 dated Jun. 1, 2016, 15 pages.
International Preliminary Report on Patentabitlity dated Jan. 10, 2014 for International Application No. PCT/AU2014/000014 (7 Pages).
International Search Report dated Jun. 2, 2014 for International Application No. PCT/AU2014/000014 (6 Pages).

* cited by examiner

DELIVERY APPARATUS, SYSTEM AND ASSOCIATED METHODS

RELATED APPLICATIONS

Priority is claimed from Australian provisional patent application no. 2014905258 filed on 23 Dec. 2014, the contents of which are incorporated by reference.

TECHNICAL FIELD

The invention relates to a medication or substance delivery apparatus, system and associated methods.

BACKGROUND

Livestock, such as cattle, often need to be administered medication substances such as vaccinations or vitamins. Typically, such medication substances are administered to the animal via a drench gun or injection gun having a needle to inject the medication substance into the animal.

The livestock industry is currently struggling with medication compliance including inaccurate dosage of medication substances, over-medication, incorrect medication and failure to adequately record delivered medication.

One reason for this struggle with medication compliance is the conditions in which medication substances are delivered to the animals where semi-skilled operators operate simple drench or injection guns to administer the medication substances. For example, the operator may incorrectly operate the drench or injection gun and may over-medicate or incorrectly the animal. Over-medication or incorrect medication may cause serious illness in the animal or at the very least may result in waste of the medication that may be expensive.

Another problem with simple drench or injection guns is that the same gun may be re-used many times with different medications which each require different dose rates and administrative procedures. Most problematically, use of the same gun with different medications may cause cross contamination which may poison or otherwise harm the animal.

In an attempt to address part of this problem semi-automatic delivery devices or guns have been proposed which, to some extent, attempt to measure and record doses of medication delivered to an animal. Typically, these devices include a gun that is configured to deliver a pre-determined dose of a medication substance to an animal. The gun may include a computer system or the like to record the delivered dose.

However, similarly to the simple drench or injection guns, these semi-automatic delivery devices or guns are still subject to medication compliance issues, in particular, the cross-contamination of medication.

The invention disclosed herein seeks to overcome one or more of the above-identified problems or at least provide a useful alternative.

SUMMARY

In accordance with a first main aspect there is provided, a hand held apparatus for delivering a substance to an animal, the apparatus including: a removable delivery section including a delivery arrangement adapted to deliver the substance to the animal; and a drive section including a drive arrangement adapted to actuate the delivery arrangement in a coupled condition in which the removable delivery section is coupled to the drive section, wherein the delivery section includes an electronic device adapted to communicate with a control system associated with at least the drive section in the coupled condition, the electronic device being configurable so to be readable by the control system such that the control system is able to identify and operate the removable delivery section.

In an aspect, the electronic device is configurable to store at least one of configuration information and substance type information.

In another aspect, the electronic device includes memory configurable to store the at least one of the configuration information and substance type information.

In yet another aspect, the control system includes a processor carried by at least one of the drive section and an external computing device, the processor being configurable to read the at least one of configuration information and substance type information thereby enabling the drive section, in association with the control system, to identify and operate the delivery section.

In yet another aspect, the control system includes a processor carried the drive section, the processor being configurable to read the at least one of configuration information and substance type information thereby enabling the drive section to identify and operate the delivery section.

In yet another aspect, the delivery section and drive section include corresponding electrical terminals arranged to electrically communicate the memory of the electronic device with the processor carried by the drive section.

In yet another aspect, the delivery arrangement includes a substance plunger and the drive arrangement includes a driving part adapted to move the substance plunger in the coupled condition.

In yet another aspect, the delivery arrangement includes a delivery coupling part coupled to the substance plunger and the drive arrangement includes a drive coupling part coupled to the driving part, wherein the delivery coupling part and driving coupling part are arranged to be releasably coupled in the coupled condition such that movement of the driving part causes like-wise movement of the substance plunger.

In yet another aspect, the delivery arrangement includes a substance reservoir and a substance piston received within the substance reservoir, and wherein the drive arrangement includes a driving part adapted to couple with the substance piston in the coupled condition so as to move the substance piston thereby moving the substance reservoir between an expanded state, in which the substance is locatable within the substance reservoir, and a contracted state in which the substance is at least partially expellable from the substance reservoir.

In accordance with a second main aspect there is provided, delivery section for removable coupling with a drive section to form a hand held apparatus for delivering a substance to an animal, the delivery section including a delivery arrangement adapted to deliver the substance to the animal and the drive section including a drive arrangement adapted to actuate the delivery arrangement in a coupled condition in which the removable delivery section is coupled to the drive section, wherein the delivery section includes an electronic identifier adapted to communicate with a control system associated with at least the drive section in the coupled condition, the electronic identifier adapted to be readable by the control system such that the control system is able to identify and operate the removable delivery section.

In an aspect, the electronic identifier includes memory configurable to store at least one of the configuration data and substance type data.

In another aspect, the delivery section includes electrical terminals arranged to electrically communicate the memory of the electronic device with a processor carried by the drive section.

In yet another aspect, the memory is electrically erasable programmable read-only memory.

In yet another aspect, the electronic identifier includes memory configurable to store data readable by the control system to determine if the delivery section is in one of a substance configured state and a non-substance configured state.

In yet another aspect, the delivery section includes: a substance cylinder in which a substance plunger is received, the substance plunger being coupled in the coupled condition with the drive arrangement; a substance inlet in fluid communication with the delivery cylinder through which the substance is selectively introducible into the delivery cylinder; and a delivery part through which the substance is selectively dischargeable to the animal.

In yet another aspect, the delivery section includes an antenna configured to read an associated identification device of the animal.

In accordance with a third main aspect there is provided, a system for delivering a dose of a substance to an animal, the system including: an interchangeable delivery section including a delivery arrangement adapted to deliver the substance to the animal and an electronic device; a drive section including a drive arrangement adapted to actuate the delivery arrangement in a coupled condition in which the interchangeable delivery section is coupled to the drive section, and a control system adapted to communicate with the electronic device and selectively operate the drive arrangement in the coupled condition, the electronic device being readable by the control system so as to enable the control system to identify and operate the interchangeable delivery section.

In an aspect, the electronic device is adapted to store delivery information and the control system is configured to receive and process the delivery information.

In another aspect, the delivery information includes data indicating if the delivery section is in one of a substance configured state and a substance non-configured state, and wherein the control system is configured to read the data and determine if the delivery section is in one of the substance configured state and the substance non-configured state.

In yet another aspect, in the substance non-configured state, the system is adapted to receive selected substance type data and determine if the selected substance type data and the delivery section are in one of a medication compatible state and a medication incompatible state.

In yet another aspect, in the medication compatible state, the control system is configured to write substance type data indicative of the selected substance to the electronic device carried by the delivery section thereby configuring the delivery section to the substance configured state.

In yet another aspect, the control system is configured to receive substance type selection data and wherein the delivery information includes delivery substance type data associated with the interchangeable delivery section, wherein the system is configured to determine if the substance type selection data and delivery substance type data represent compatible substances, and restrict operation of the system if the substances are incompatible.

In yet another aspect, the control system is configured to receive substance type selection data and wherein the delivery information includes delivery section type data indicating the type of coupled interchangeable delivery section, wherein the control system is configured to determine if the substance type selection data and delivery section type data represent a compatible combination, and restrict operation of the system if the combination is not compatible.

In accordance with a fourth main aspect there is provided, a method for determining medication compatibility of a delivery section adapted to couple in a coupled condition with a drive section to form a hand held medication delivery apparatus, the method including the steps, in a processing system associated with the hand held medication delivery apparatus, of: Receiving, from an electronic device carried by the delivery section, delivery medication type data representing a delivery medication type associated with the delivery section; Receiving, selected medication type data representing a selected medication type selected for use; Determining, compatibility of the delivery medication type and the selected medication type to provide compatibility data representing at least one of a compatible medication state and an incompatible medication state; and wherein, in the incompatible medication state, the processing system is configured to at least partially disable operation of the medication delivery apparatus so as to inhibit delivery of medication.

In accordance with a fifth main aspect there is provided, a method for configuring a delivery section adapted to couple in a coupled condition with a drive section to form a hand held medication delivery apparatus, the method including the steps, in a system associated with the hand held medication delivery apparatus, of: Receiving, from an electronic device carried by the delivery section, delivery data; Determining, if the delivery data indicates the delivery section is in one of a medication configured state and a medication non-configured state; wherein, in the medication non-configured state, the system is adapted to receive selected medication type data and determine if the selected medication type data and the delivery section are in one of a medication compatible state and a medication incompatible state.

In an aspect, in the medication compatible state, the method includes the step of writing medication type data indicative of the selected medication to the electronic device carried by the delivery section thereby configuring the delivery section to the medication configured state.

In another aspect, the electronic device includes a memory device, and wherein the step of writing medication type data includes writing the medication type data to the memory device and configuring the memory device to a locked state such that the medication type data cannot be normally overwritten.

In yet another aspect, in the medication non-configured state, the system is configured to determine a connected delivery section type associated with the delivery section, and determine if the selected medication type data is compatible with the connected delivery section type.

In yet another aspect, in the medication non-configured state, the system is configured to determine delivery section medication type data associated with the delivery section, and determine if the selected medication type data is compatible with the delivery section medication type data.

In accordance with a sixth main aspect there is provided, a method for determining medication compatibility of a delivery section adapted to couple in a coupled condition with a drive section to form a hand held medication delivery apparatus, the method including the steps of: Reading, delivery medication type data from an electronic device carried by the delivery section, the delivery medication type data representing a delivery medication type associated with the delivery section, Receiving, at a control system in communication with the delivery section, the delivery medication type data; Receiving, at the control system, a selected medication type data representing a selected medication type selected for use; Determining, via the control system, compatibility of the delivery medication type and the selected medication type to provide compatibility data representing at least one of a compatible medication state and an incompatible medication state; and wherein, in the incompatible medication state, the control system is configured to at least partially disable operation of the medication delivery apparatus so as to inhibit delivery of medication.

BRIEF DESCRIPTION OF THE FIGURES

The invention is described, by way of non-limiting example only, by reference to the accompanying figures, in which.

DETAILED DESCRIPTION

Figure 1:
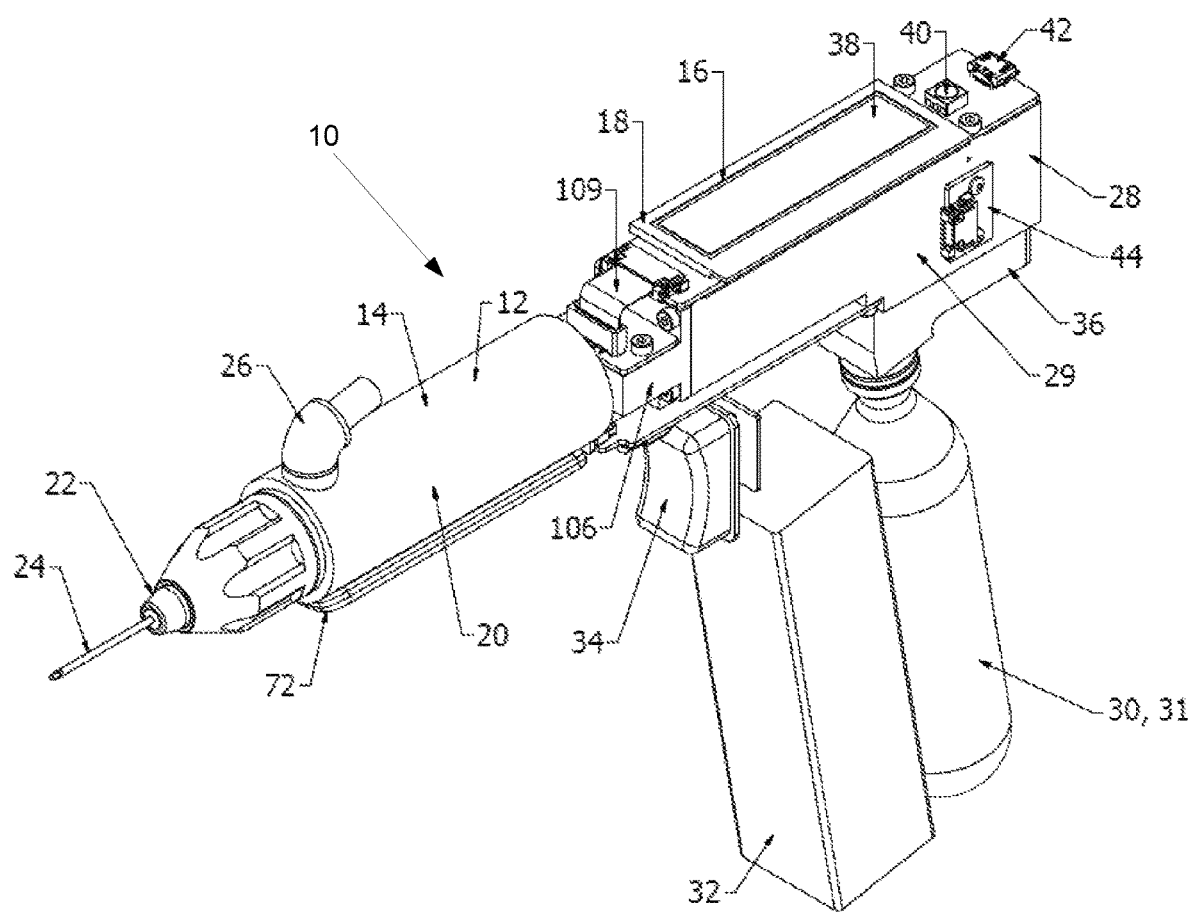
FIG. 1 is a front perspective view illustrating a hand held apparatus including a front delivery section and a rear hand held drive section in a coupled condition.
Figure 2:
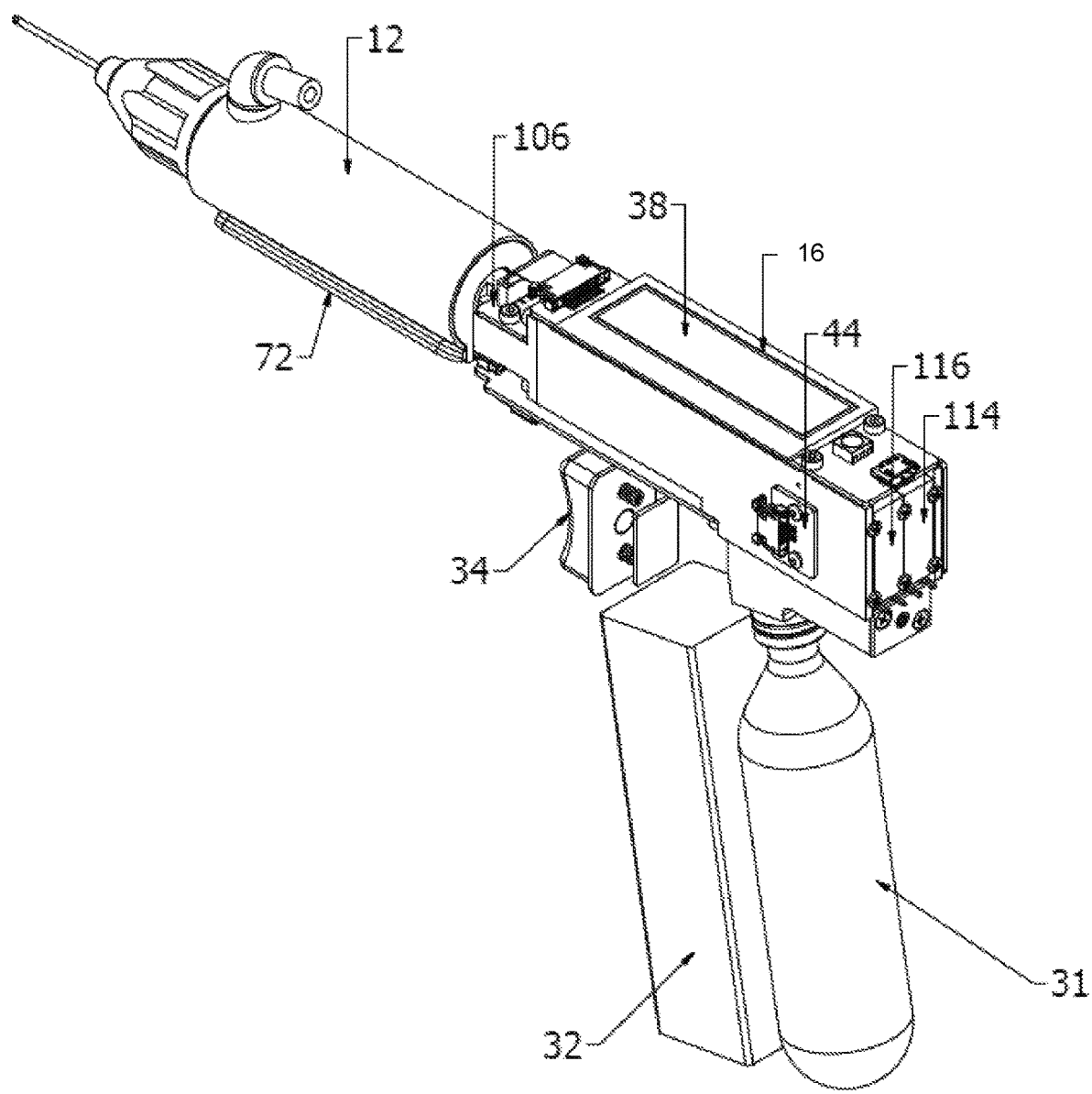
FIG. 2 is a rear perspective view illustrating the hand held apparatus including the front delivery section and the rear hand held drive section in the coupled condition.

Referring to FIGS. 1 and 2, there is shown a first example of a hand held apparatus 10 for delivering a substance such as a medication or vitamin to an animal. The apparatus 10 includes a removable delivery section 12 including a delivery arrangement 14 (shown best in FIG. 8) adapted to deliver the substance to the animal and a drive section 16 including a drive arrangement 18 (shown best in FIG. 8). The delivery section 12 and drive section 16 are moveable between a coupled condition, in which the delivery section 12 and drive section 16 are coupled to one another such that the drive arrangement 18 is able to actuate the delivery arrangement 14, and a decoupled condition in which the delivery section 12 and drive section 16 are detached from one another.

Figure 3:
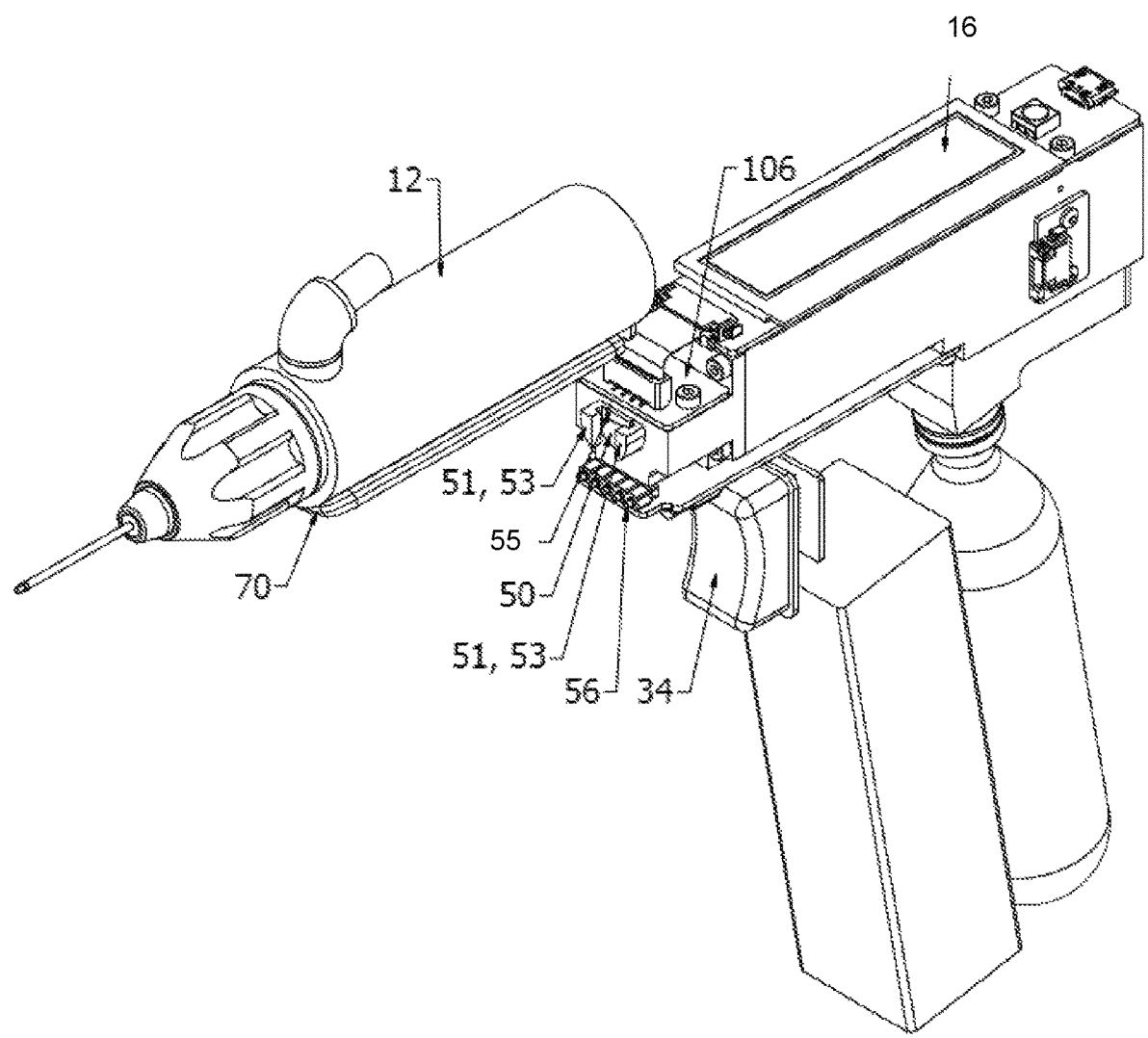
FIG. 3 is a front perspective view illustrating a hand held apparatus including a front delivery section and a rear hand held drive section in a de-coupled condition.
Figure 4:
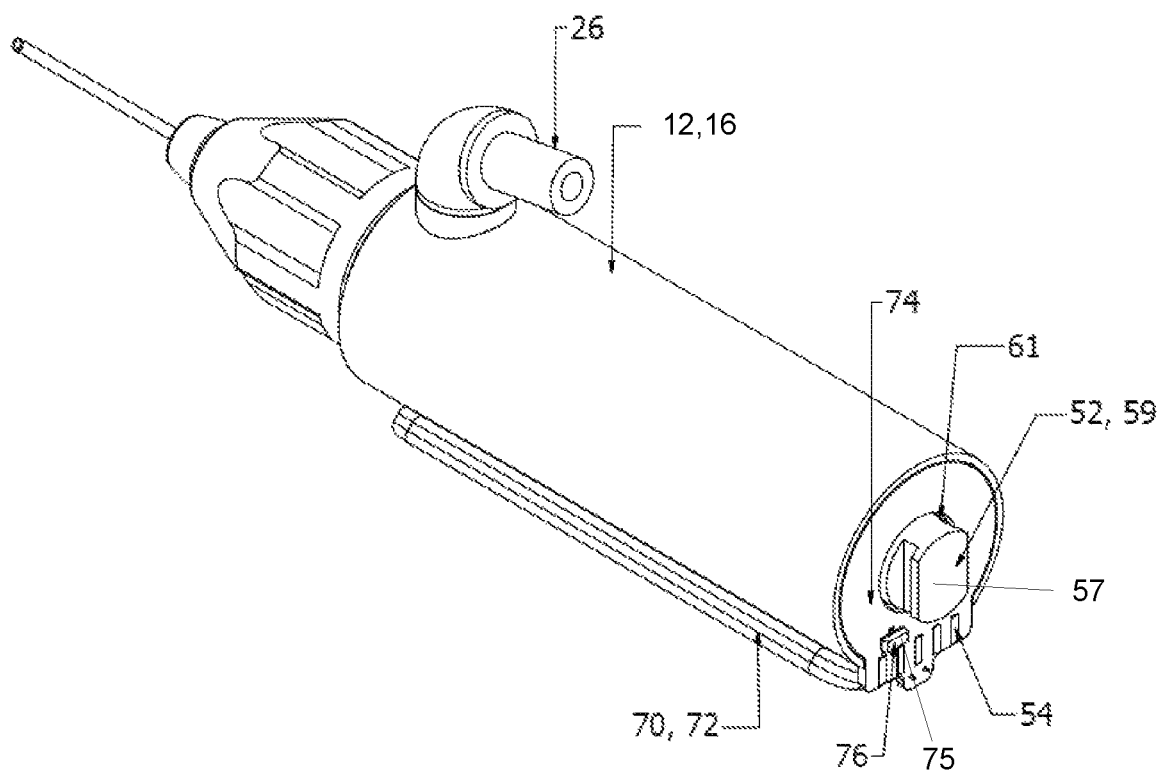
FIG. 4 is a rear perspective view illustrating the front delivery section.

The delivery section 12 includes a body 20 which houses the delivery arrangement 14 and a delivery part 22 which is provided in this example in the form of a needle 24 extending therefrom. However, the delivery part 22 may take other forms such as a drench tube or other suitable medication delivery fitting. The delivery section 12 is an interchangeable and reusable unit or adaptor that may be moved to a de-coupled condition as shown in FIGS. 3 and 4. The delivery section 12 includes a substance or medication inlet 26 to which a line or tube is connectable to supply the substance to the delivery section 12.

The drive section 16 is arranged to couple with and control the delivery section 12 in the coupled condition. The drive section 16 includes a body 28 having a manifold 29 arranged to house the drive arrangement 18, a pressurised gas vessel 30 coupled to the body 28, a battery 32 to power the on-board electronics of the drive section 16 and the delivery section 12, and a trigger 34 arranged to be actuated by a user. The pressurised gas vessel 30 is provided in the form of an interchangeable pre-pressurised Carbon-Dioxide canister 31 which is relesably coupled to the body 28 via a gas regulator 36. It is noted that some examples of the apparatus, such as a second example shown below in FIGS. 9 to 18 may include an electrical or mechanical drive arrangement and as such do not include pneumatic components such as the pressurised gas vessel 30.

The drive section 16 further includes a display 38 for displaying information to a user, visual indicator lights 40 for indicating the apparatus 10 status as well as a USB data connector 42 and a pressure sensor 44 arranged to measure pressure within or associated with the gas regulator 36 or canister 31.

Figure 5:
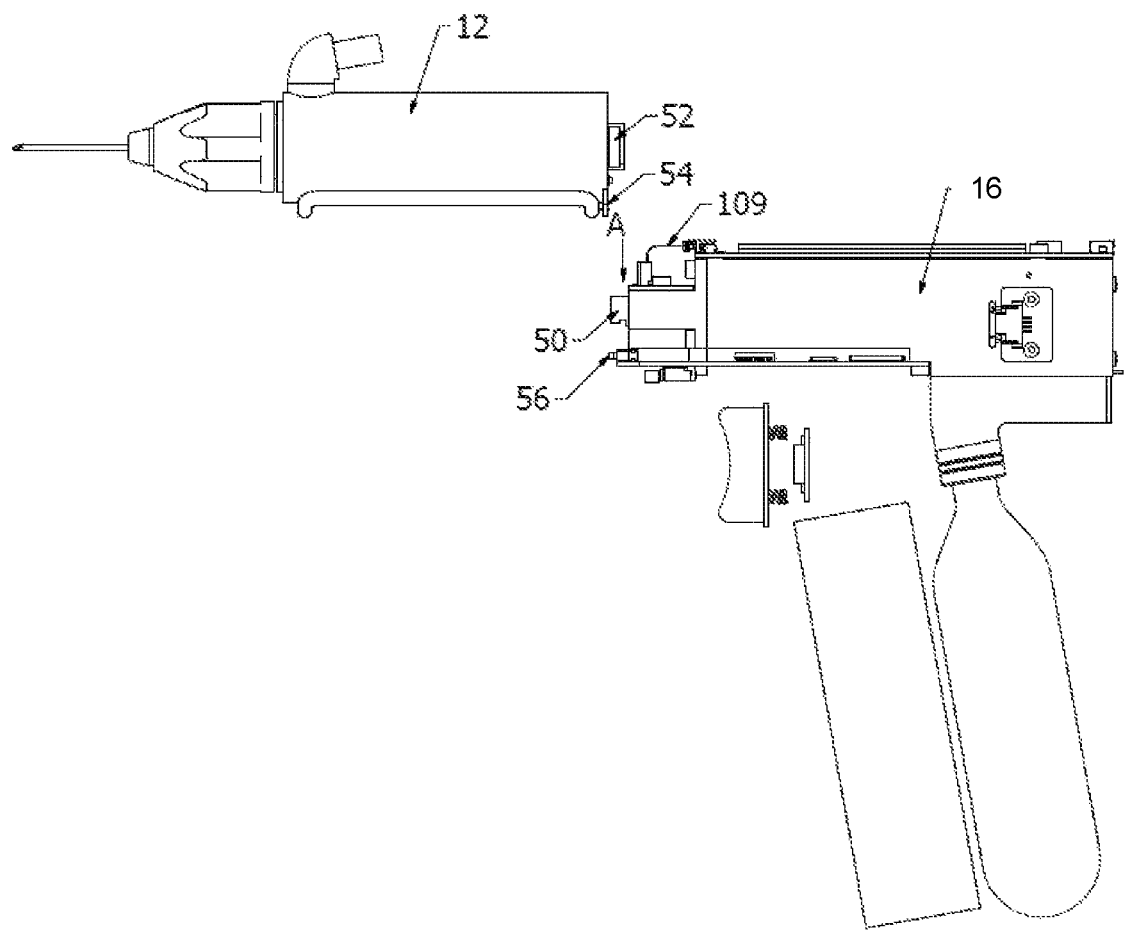
FIG. 5 is a side view illustrating the hand held apparatus in the de-coupled condition.

Referring now more specifically to FIGS. 3 to 5, the drive section 16 includes a drive coupling part 50 which is arranged to releasably coupled with a correspondingly arranged delivery coupling part 52 carried by the delivery section 12. In this example, the coupling part 50 is shown as a female part arranged to receive the male coupling part 52. However, the arrangement may be reversed to achieve the same functionality.

The coupling part 50 and the coupling part 52 are arranged to couple with one another in a manner so as to allow the drive arrangement 18 to actuate the delivery arrangement 14 in both a forward and reverse direction as will be further described below with reference to FIG. 8.

The delivery coupling part 52 is slidably received by the drive coupling part 50 in a vertical direction (shown by arrow "A" in FIG. 5) and may be adapted to snap fit with one another so as to be at least temporarily secured in the coupled condition. More specifically, the drive coupling part 50 includes opposing sides 51 and each opposing side 51 includes a projecting lip 53 which defines a vertically arranged slot or channel 55. The delivery coupling part 52 includes projecting body 57 having an end flange 59 and opposing slot or channel 61. In the coupled condition, the end flange 59 is received by the slot or channel 55 of drive coupling part 50 and the projecting lips 53 of the drive coupling part 50 are received by the opposing slots 61 of the delivery coupling part 52.

The delivery section 12 includes delivery electrical or signal connectors 54 and the drive section 16 include corresponding electrical or signal connectors 56 which are arranged to communicate with the delivery connectors in the coupled condition. In this example, the drive electrical connectors 56 are slide connector pins and the delivery electrical connectors 54 are slide pads arranged align and communicate with the slide connector pins in the coupled condition. Accordingly, the delivery electrical connectors 54 and drive electrical connectors 56 slide into engagement when the coupling parts 50, 52 are slid into engagement with one another. The drive section 16 further includes a position sensor 106 and a flexible circuit connector 109 which interconnects the electrical or signal connectors 56, the display and the position sensor 106.

The delivery section 12 further includes an antenna 70 provided in the form of an Radio Frequency Identification Device (RFID) antenna 72 extending at least partially along an underside of the delivery section 12. The delivery section 12 also carries further electronic and control components, provided in the form of an electronic device or identifier 75 including a memory device 76 connected to a Printed Circuit Board (PCB) 74. The memory device 76 may be provided in the form of an EEPROM (Electrically Erasable Programmable Read-Only Memory Chip) which may be pre-programed with configuration and operational data associated with the type and use of the delivery section 12. The memory device 76 may also be programmed with a medication type code when the delivery section 12 is first coupled to the drive section 16 and configured for use as will be further described below. In other examples, the electronic device or identifier 75 may take other forms to identify the particular delivery section 12 connected or proximate to the drive section 16.

Figure 6:
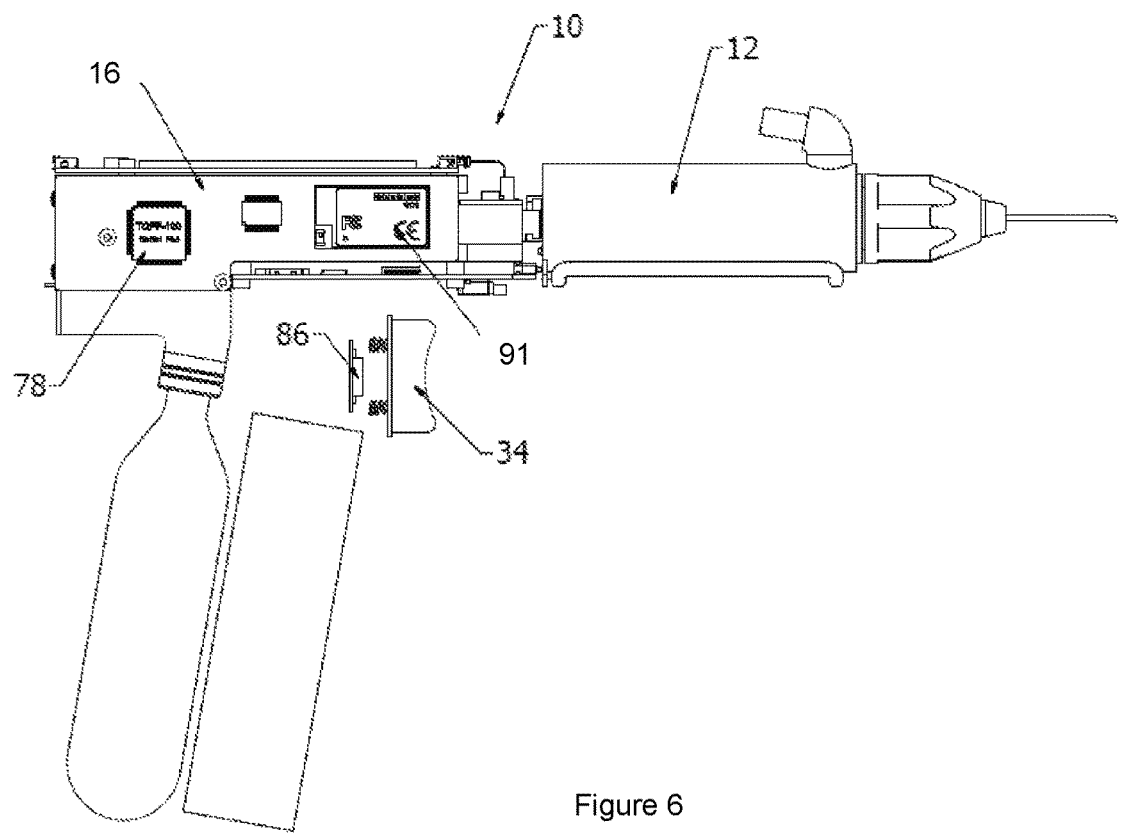
FIG. 6 is a side view illustrating the hand held apparatus in the coupled condition.
Figure 7:
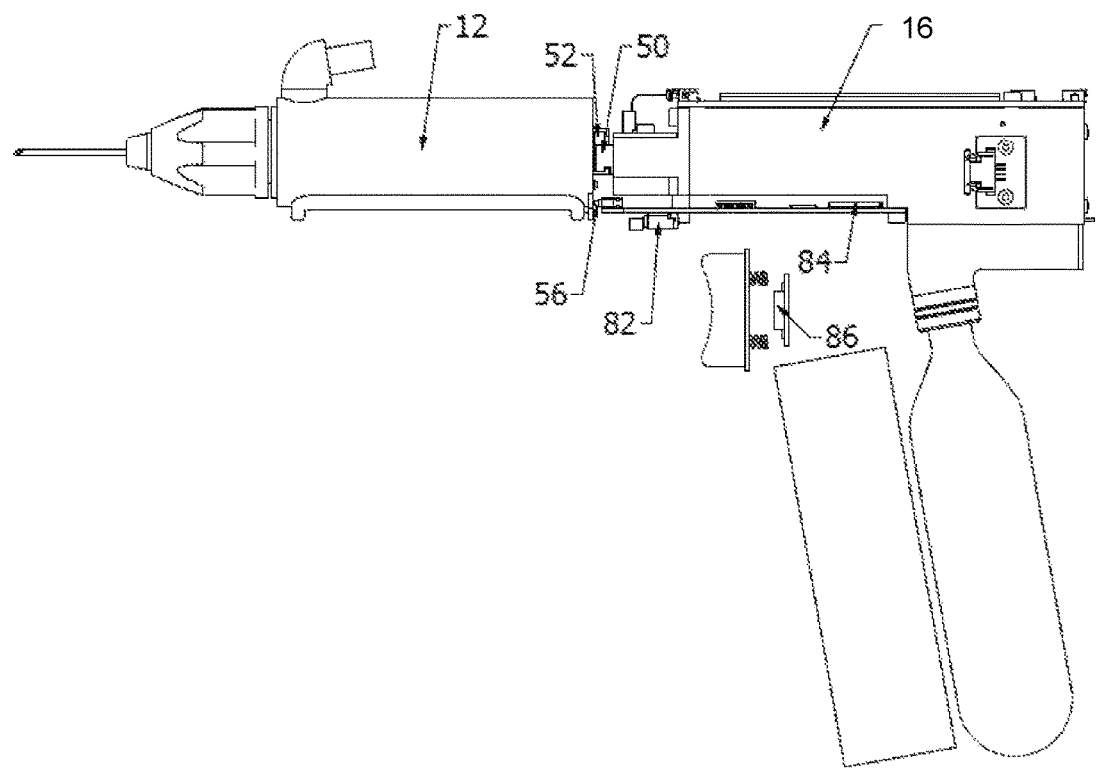
FIG. 7 is an opposing side view illustrating the hand held apparatus in the coupled condition.

Referring more specifically to FIGS. 6 and 7 the drive section 16 includes a processor 78 that is part of a control system 200, further described below, which operates the apparatus 10. The drive section 16 also includes a WiFi module 80, a vibration motor 82 configured to vibrate to signal functions or alerts to a user, further memory devices 84 such as an SD card and a reed switch 86 positioned behind and configured to detect actuation of the trigger 34.

Figure 19A:
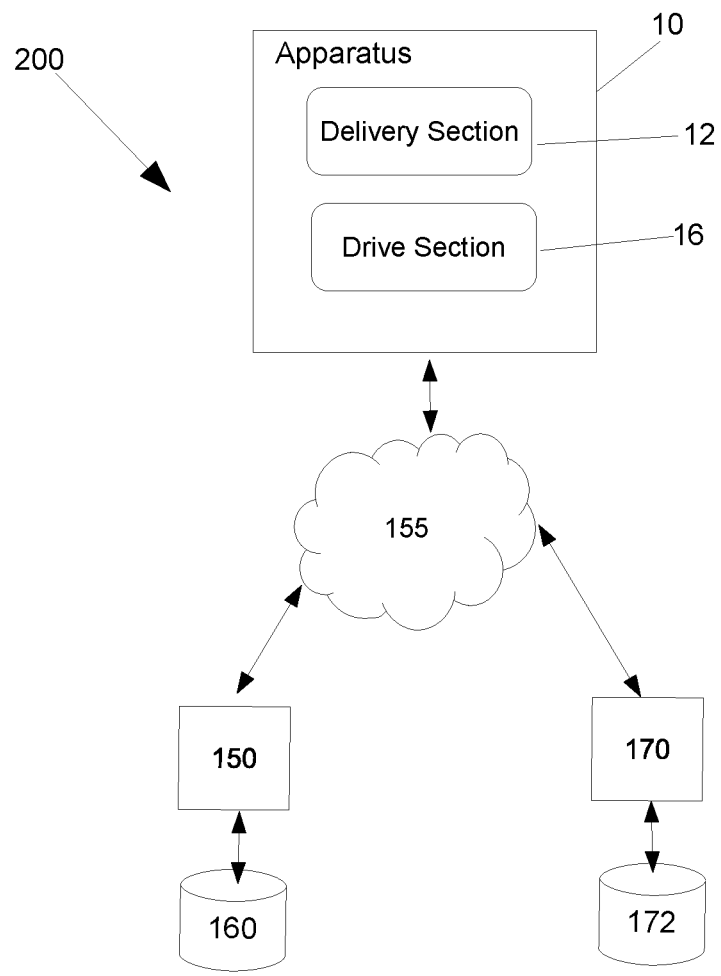
FIG. 19a is a simplified block diagram of a system for operation of the hand held apparatus.
Figure 19B:
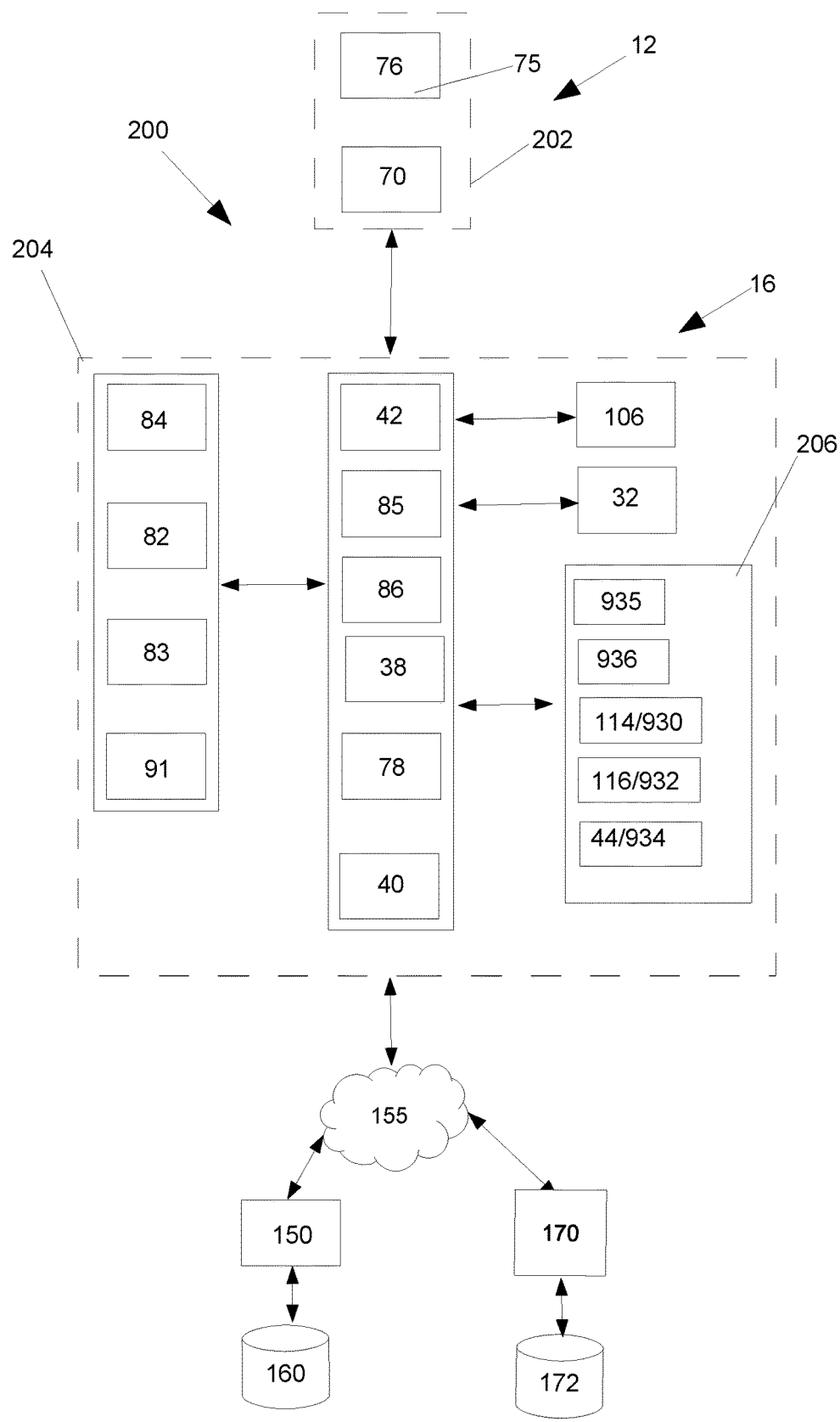
FIG. 19b is a more detailed block diagram of the system for operation of the hand held apparatus.

The interaction of the processor 78 and other components of the apparatus 10 are further described below with reference to the system block diagram as shown in FIGS. 19a and 19b.

It is noted that FIGS. 1 to 8 show the apparatus 10, in particular the drive section 16, without an outer body housing or casing which supports, protects, covers and locates the relevant parts and components. The outer body housing or casing may also be arranged to serve aesthetic proposes and provide a gun shaped handle. Accordingly, any commercial forms of the apparatus 10 may also include such as outer body housing or casing. An example of a suitable casing is illustrated in relation to a second example of the apparatus 10 in FIG. 9.

Figure 8:
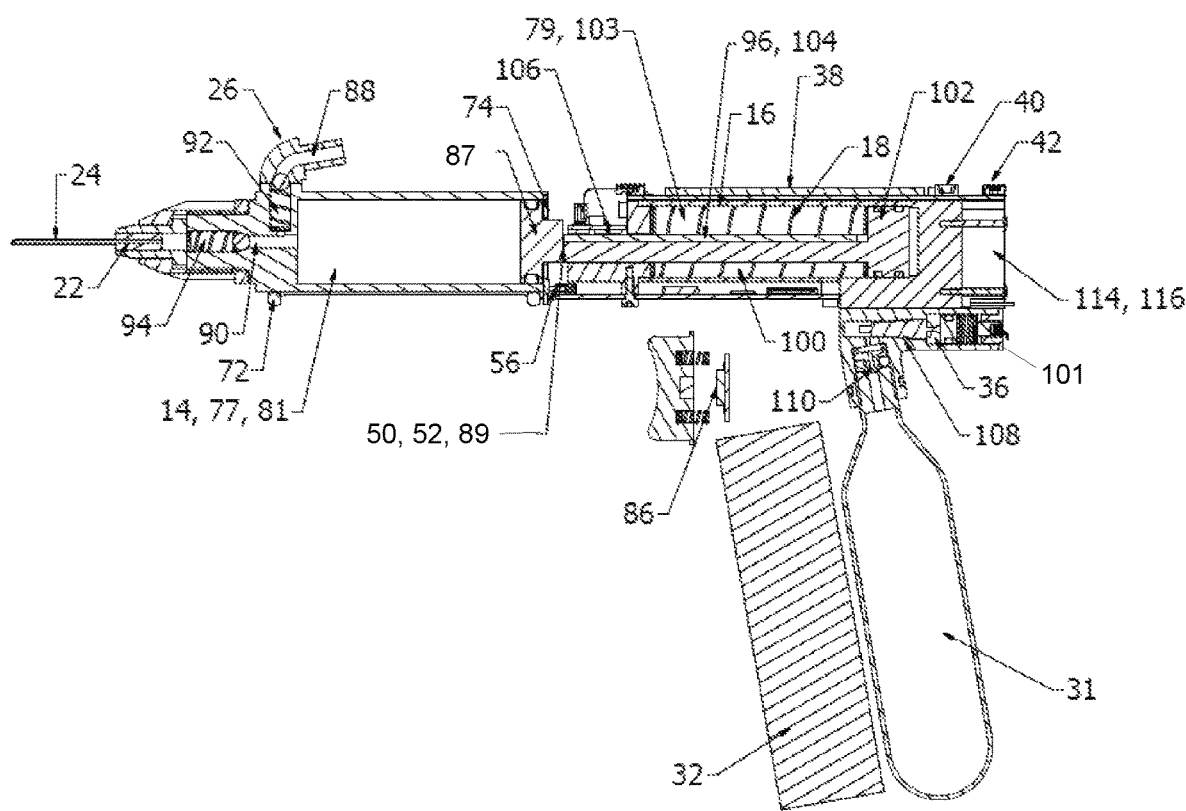
FIG. 8 is a sectional view opposing side view illustrating the hand held apparatus in the coupled condition.
Figure 9:
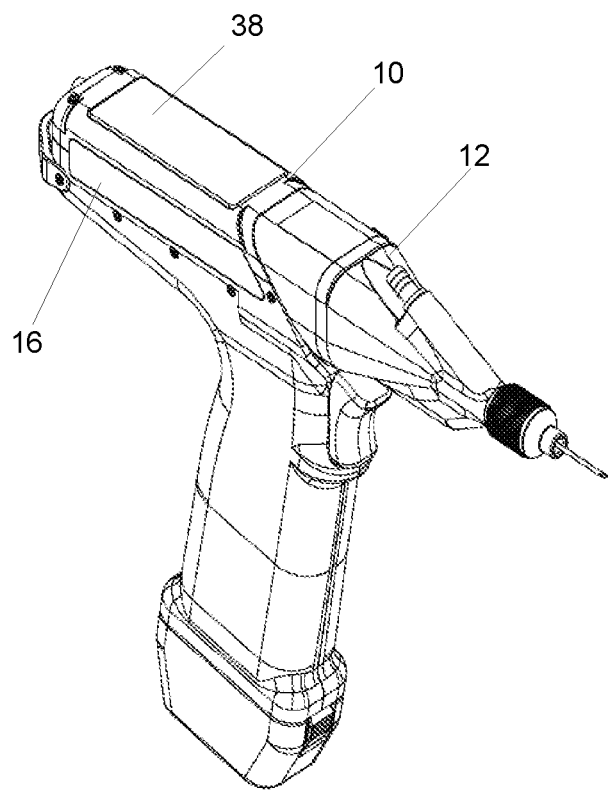
FIG. 9 is a front perspective view illustrating a second example of a hand held apparatus including a front delivery section and a rear hand held drive section in a coupled condition.

Referring now to FIG. 8, the internal structure of the apparatus 10 is shown in more detail. The delivery arrangement 14 includes a delivery cylinder 81 and a substance plunger 80 slidably received and arranged to seal with the delivery cylinder 81. The substance plunger 80 includes a piston head 87 and a shaft 89 that extends from the piston head 87 and terminates at the delivery coupling part 52 which is carried by the shaft 89. It is noted that in this example the shaft 89 is short and in some examples, the piston head 87 may coupled directly to the delivery coupling part 52 without a defined shaft as such.

The delivery cylinder 81 provides a medication reservoir 77 that is moved between an expanded condition, in which medication is drawn into the medication reservoir 77 by the substance plunger 80, and a contracted condition in which the medication reservoir 77 is moved to a contracted condition by the substance plunger 80 to expel medication from the medication reservoir 77.

The medication inlet 26 is in fluid communication with the delivery cylinder 81 via an inlet conduit 88 that is connected to a main delivery conduit 90. The inlet conduit 88 includes a one-way valve 92 arranged to allow fluid medication substances to flow into the main delivery conduit 90 and into the delivery cylinder 81. The main delivery conduit 90 also includes a one-way valve 94 between the inlet conduit 88 and the delivery part 22 that is arranged in a reverse configuration relative to the one-way valve 92 so as to allow flow of fluid medication substances from the delivery cylinder 81 to the delivery part 22.

The drive arrangement 18 of the drive section 16 includes a driving part 96 adapted to move the substance plunger 80 in the coupled condition. In this example, the driving part 96 is provided in the form of a drive plunger 98 received by a drive cylinder 100 of the drive arrangement 18. The drive plunger 98 includes a drive piston 102 and a drive shaft 104 extending from the drive piston 102. The free end of the drive shaft 104 includes the drive coupling part 50. Accordingly, in the coupled condition, movement of the drive plunger 98 causes like-wise movement of the substance plunger 80. A spring 103 is concentrically fitted to the drive shaft 104 between the drive piston 102 and an inner front wall 107 of the drive cylinder 100. The spring 103 urging or biasing the drive plunger 98 in a retracted or rearward position as is shown in FIG. 7.

The drive section 16 includes the position sensor 106 configured to measure the position of the shaft 104 relative to the fixed sensor 106. In this example, the sensor 106 is a linear encoder through which the shaft 104 passes and the shaft 104 includes encoder readable portions arranged to allow accurate positional measurement of the movement of the shaft 104. The encoder is located between the drive cylinder 100 and the drive coupling part 52 located at the forward end 17 of the drive section 16. The sensor 106 is in communication with the control system 200 as is further described below.

The drive arrangement 18 is powered by a pneumatic system 104 that includes the canister 31 and a pneumatic housing or manifold 108. However, as is detailed below with the second example, the drive arrangement 18 may also include or be powered by an electric motor or the like. Other suitable drive arrangements may also be utilised.

The pneumatic housing 108 includes an inlet coupling 110, a regulator 36, an inlet valve 114 and an exhaust valve 116. The inlet coupling 110 is adapted to releasable receive, attach and pierce the canister 31. The inlet coupling 110 may be a threaded coupling which carries a central pin to pierce a seal of the canister 31. The regulator 36 is located between the inlet coupling 110 and the inlet valve 114 to regulate flow of the pressured gas into the drive cylinder 100. The inlet valve 114 and the exhaust valve 116 are electronic control valves controlled by the control system 200.

The drive cylinder 100 provides a drive reservoir 79 which is moved between an expanded condition, in which pressured gas is introduced into the drive reservoir 79 by the pneumatic system 101 which drives or moves the drive plunger 98 to cause likewise movement of the substance plunger 80, and a contracted condition in which the drive reservoir 79 is moved by the spring 103 which urges the drive plunger 98 rearward in the drive cylinder 100 and expelling the gas via the exhaust valve 116.

Second Example of the Apparatus

Referring now to FIGS. 9 to 18, there is disclosed a second example of the apparatus 10 in which like numerals are used to denote like parts. The second example is a preferred form of the apparatus 10.

This second example of the apparatus 10 is similar to the first example in its overall configuration and operation. Accordingly, all parts and functionalities are not again described here in detail. However, some of the differences are detailed below including differences in the drive arrangement 18 of the drive section 16 that now includes a linear electric drive system rather than a pneumatic drive system.

Figure 13:
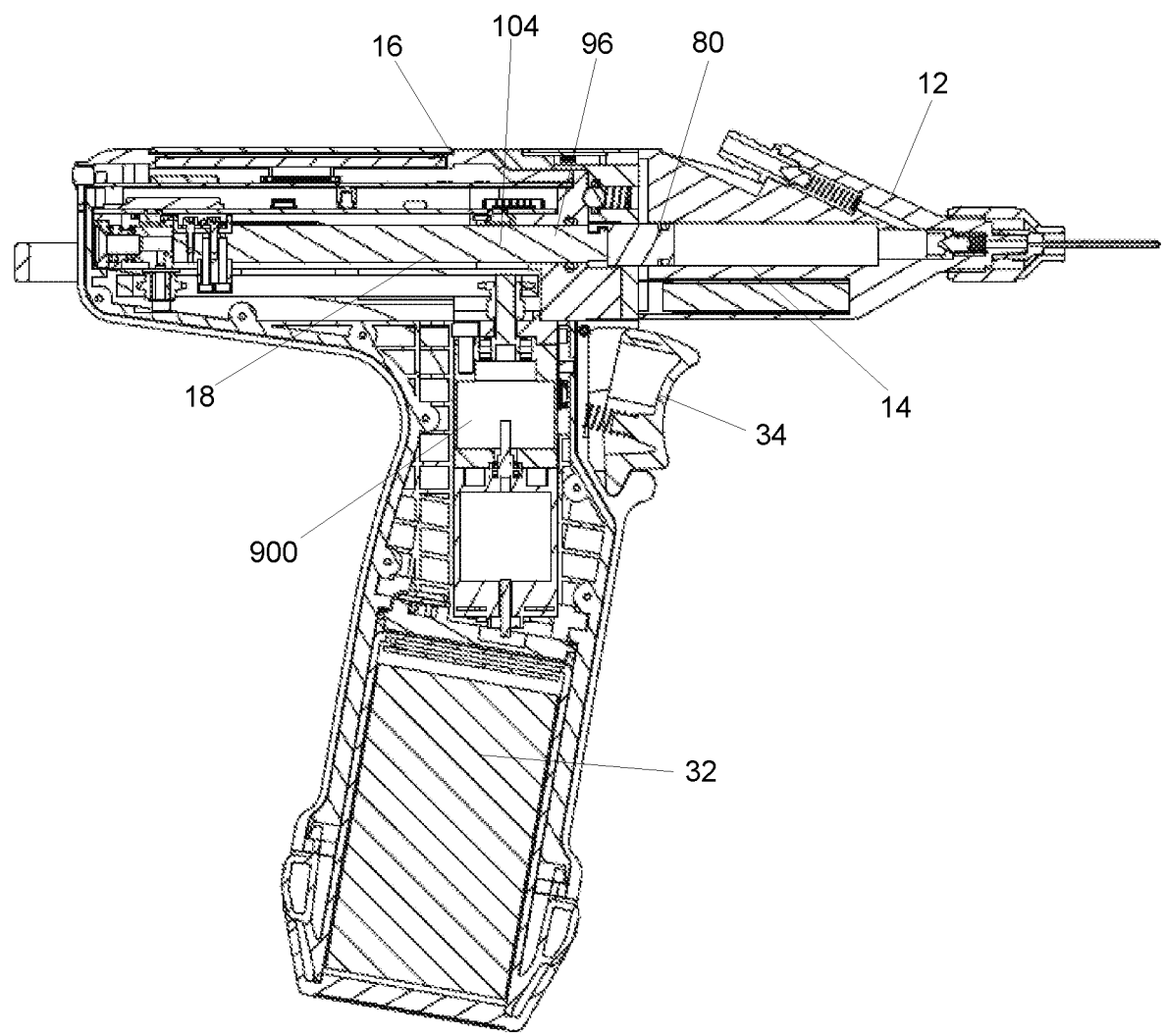
FIG. 13 is a cross sectional side view illustrating the hand held apparatus including the front delivery section and the rear hand held drive section in the coupled condition.
Figure 14:
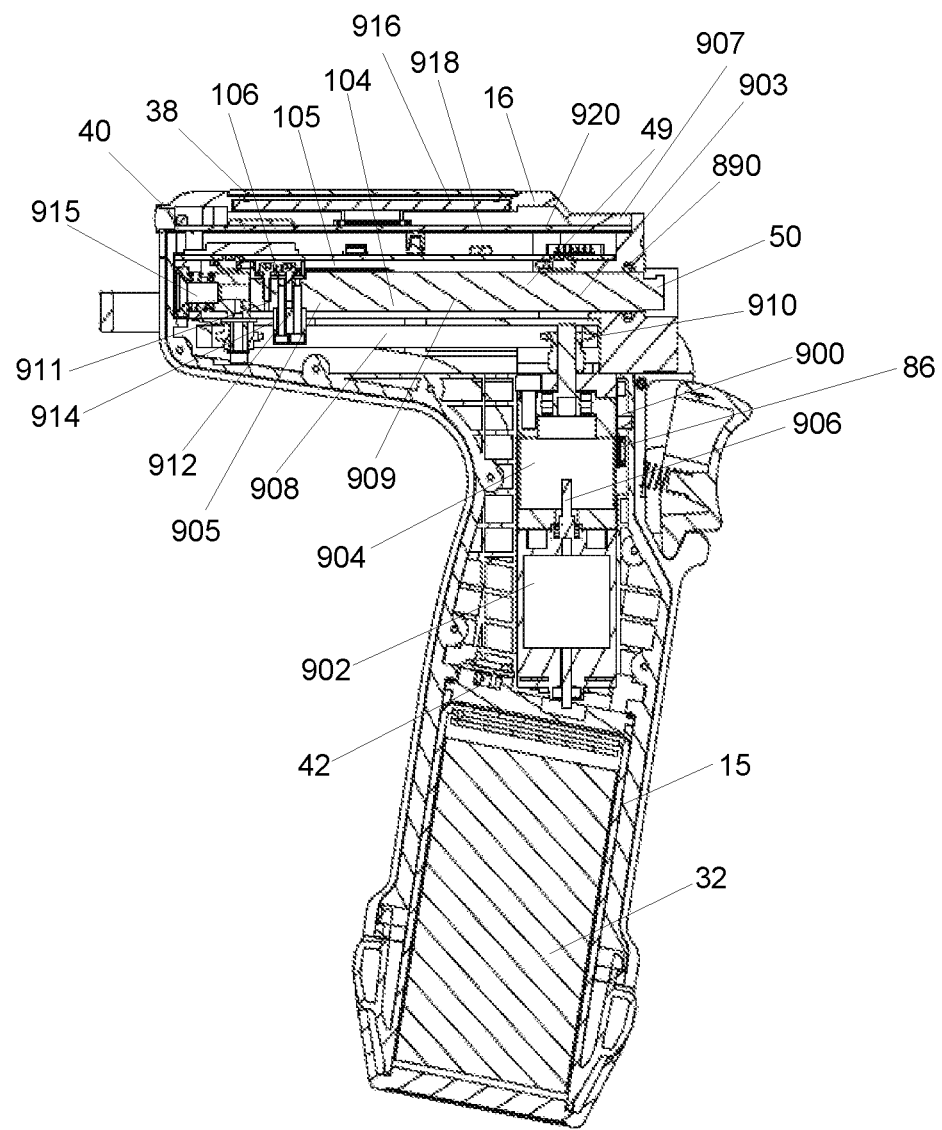
FIG. 14 is a cross sectional side view illustrating the rear drive section with the front delivery section in the de-coupled condition.
Figure 15:
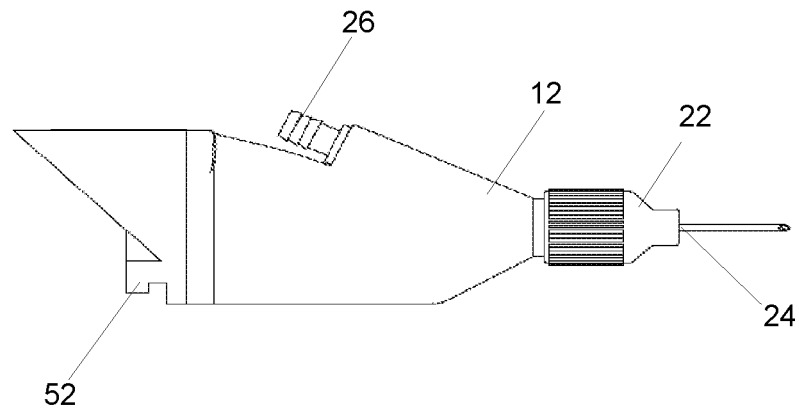
FIG. 15 is a side view illustrating the second example of the front delivery section.
Figure 16:
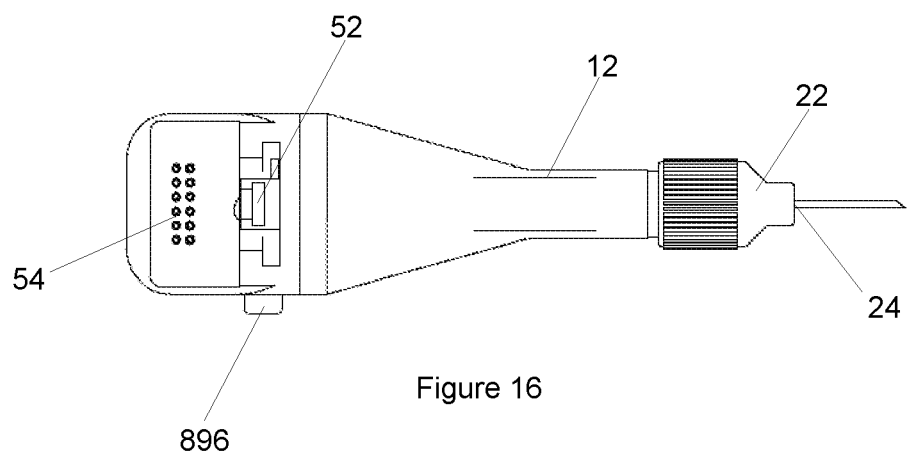
FIG. 16 is a bottom view illustrating the second example of the front delivery section.
Figure 17:
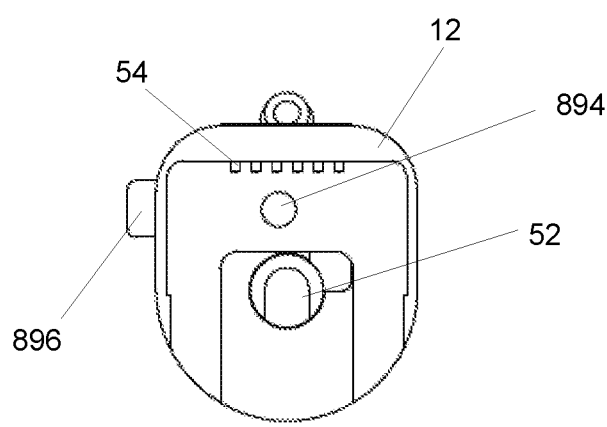
FIG. 17 is an end view illustrating the second example of the front delivery section.
Figure 18:
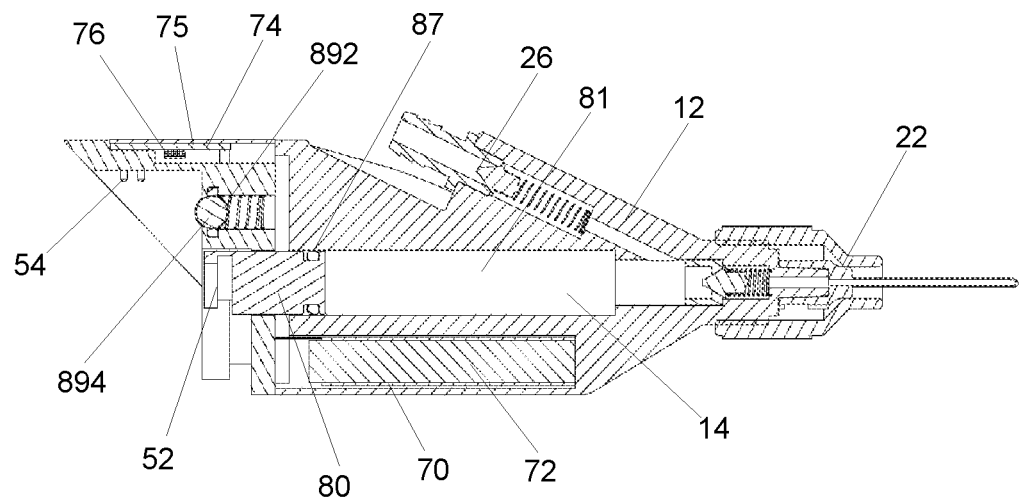
FIG. 18 is a cross sectional side view illustrating the front delivery section.

Turning to firstly the drive section 16 and referring more specifically to FIGS. 13 and 14, in this example the drive arrangement 18 of the drive section 16 includes a driving part 96 adapted to move the substance plunger 80 in the coupled condition. In this example, the driving part 96 is provided in the form of a shaft 104, preferably a pin or rod shaped shaft, arranged lengthwise within the drive section 16. The shaft 104 is linearly actuated by a linear drive arrangement 900 that linearly moves the shaft 104 in a forward and reverse direction. Accordingly, in the coupled condition, movement of the drive rod 104 causes like-wise movement of the substance plunger 80 of the delivery section 12. The shaft 104 includes a seal 890, preferably an O-ring seal, between the main body 49 of the shaft 104 and the coupling part 50.

The drive section 16 includes the position sensor 106 configured to measure the position of the shaft 104 relative to the position sensor 106. In this example, the sensor 106 is a linear encoder positioned proximate the shaft 104 and the shaft 104 includes encoder readable portions 105 arranged to allow accurate positional measurement of the movement of the shaft 104. The sensor 106 is in communication with the control system 200, as is further detailed below.

In this example, the linear drive arrangement 900 includes a high torque electric motor 902, located in the handle portion 15 of the drive section 16, that is coupled to the shaft 104 by a coupling arrangement 906. The coupling arrangement 906 includes a gearbox 904, preferably a planetary gearbox, that reduces the speed of the motor 902, and a drive sprocket 910 positioned immediately beneath the front end 903 of the shaft 102 within forward end 907 of the main body 909 of the drive section 16.

The coupling arrangement 906 further includes second or idler sprocket 912 located at an opposing end 911 of the main body 909 of the drive section 16 toward the trailing end 905 of the shaft 104, and a micro-chain 908 that extends around sprockets, 910, 912 and is driven, in a forward and reverse direction by the drive sprocket 910. In some examples, the micro-chain 908 may be replaced with a timing belt or similar part. The coupling arrangement 906 includes adjustment features including a spring tensioner 914 for the idler sprocket 912 and a chain tensioning screw 915.

The shaft 104 is coupled along one side or top of the chain 908 so at to be moveable therewith in a linear forward and reverse direction. In use, the electric motor 902 is operated by the control system 200 to actuate the shaft 104 via the linear drive arrangement 900 and thereby actuating the substance plunger 80 of the delivery section 12 in the coupled condition.

In this example, the drive section 16 also includes a control and interface arrangement 916 provided in the form of a first board arrangement 918 and a second board arrangement 920. The first board arrangement 918 includes a processor 78, RFID control unit & communication circuits 85. The second board arrangement 920 includes a WI-FI module 80, flash memory 84, vibration motor 82, indicator buzzer 83, motor drive 930, voltage regulators 932, zero position switch 934 and maximum position switch 936 (shown in FIG. 19b). These components are further detailed in system diagrams 19a and 19b below. The drive section 16 also includes an indicator light 40, a display 38, a battery 32, and an USB I/O port 42.

Referring now more specifically to FIGS. 15 to 18, the second example of the delivery section 12 is shown in greater detail. The second example of the delivery section 12 couples to the drive section 14 in a similar to way as described in the first example. Accordingly, the second example of the delivery section 12 includes a similar delivery arrangement 14 including a delivery cylinder 81 and a substance plunger 80 slidably received and arranged to seal with the delivery cylinder 81. The substance plunger 80 includes a piston head 87 and is coupled to the delivery coupling part 52.

The delivery section 12 includes delivery electrical or signal connectors 54 in the form of slide connector pins. The delivery section 12 carries further electronic and control components, provided in this example in the form of the electronic device or identifier 75 connected to or supported by a Printed Circuit Board (PCB) 74. The electronic device or identifier 75 preferably includes a memory device 76 provided in the form of an EEPROM Chip which may be pre-programed or pre-configured with configuration or operational data (also known as "factory settings data") associated with the type and use of the delivery section 12. For example, the pre-programed data may include delivery section type data that relates to the type of delivery section 12, volume data such as minimum and maximum dose and other parameters that relate to the operation of the delivery section 12.

In other examples, the pre-programed data may simply be a delivery section code unique to a particular delivery section 12 or type of delivery section, the code may then be read by the system 200 as is further described below to load the configuration and operational data. It is also noted that the memory device 76 may also be programmed and locked with a selected medication type code when the delivery section 12 is first coupled to the drive section 16 and configured for use as will be further described below. This, in effect, locks the delivery section 12 to a particular medication type.

In this example, the delivery section 12 also includes a releasable locking arrangement 892 to releasable secure the delivery section 12 to the drive section 16. The releasable locking arrangement 892 includes a lock mechanism 894 and an actuator 896 in the form of a button (shown best in FIG. 16). In use, the releasable locking arrangement 892 snap locks in the coupled condition to secure the delivery section 12 to the drive section 16 together. The actuator 896 may then be depressed to release the locking arrangement 892 thereby allowing the delivery section 12 to be removed.

Turning now to FIGS. 19a and 19b, the control system 200 (also referred to as "the system") is now described in further detail. In the example, below the control system 200 is described in common primarily with reference to the first example. However, the control system 200 generally functions similarly in both of the above-described first and second examples with the main differences being the operation and control of drive arrangements 18 and the related components.

The control system 200 associated with the apparatus 10 includes components carried by the delivery section 12 and the drive section 16. In this example, the control system 200 may also interface with or include external computing devices 150 which perform some of the data processing, provide inputs and store outputs from the apparatus 10. However, the apparatus 10 may in some examples be provided to integrally include the functionality of such an external computing devices 150 and in these examples such an external computing device 150 may not be required.

In some examples, the computing device 150 may be a mobile computing device, such as a smart phone or tablet, loaded with application software configured to communicate over a network, internet or wireless connection 155 with the apparatus 10. The external computing device 150 may include or communicate with and an external database 160 and, and may be configured to perform many or most of the processing steps of the methods disclosed herein. The external computing device 150 may carry one or more further processors or memory devices. In other examples, external computing device 150 may also be in the form of a webserver or computer system in communication with a database 160 from which the apparatus 10 may retrieve and store information. In some examples, the computing device 150 or the apparatus 10 may communicate with a server system 170 and server database 172. Such computing devices 150 and server systems 170 are well known and are not described here in any detail.

In more detail, and referring now to FIG. 19b, the parts of the control system 200 carried by the apparatus 10 are disclosed in more detail. Firstly, the delivery part 12 includes delivery control components 202 including the antenna 70 and the electronic device 75 including the memory device 76 which are communicated with the parts of the control system 200 carried by the drive section 16 in the coupled condition.

The drive section 16 includes drive control components 204 that may be arranged in a of variety configurations on PCB boards within the drive section 16. The drive control components 204 include the processor 78 configured to read the memory device 76, the communication WiFi module 91, the USB data device 42, the battery 32, the trigger read switch 86, the vibration motor 82, an audible buzzer 83, an RFID antenna circuit 85 in electrical communication in the coupled condition with the antenna 70, a position senor 106 which communicates with the processor 78, the display 38 and the indicator lights 40.

The drive control components 204 include as identified by 206 some components that are different between the first and second examples of the apparatus 10. The pressure sensor 44, for example, is replaced with a motor current sensor 934 in the second example, and the pneumatic valves 114, 116 are replaced respectively by the voltage regulator 930 and the current regulator 932 in the second example of the apparatus 10. The first and/or second examples may also be fitted with the zero position switch 935 and the maximum position switch 936.

The reed switch trigger 86, the battery 32 and the inlet pneumatic control valve 114 and the outlet pneumatic control valve 116 (replaced respectively by a voltage regulator 930 and a current regulator 932 in the second example of the apparatus 10) are each in electrical communication with the processor 78. The processor 78 may be in the form of a microcontroller and include multiple processing units and associated memory to store software code executable by the processor 78 to operate the apparatus 10 in accordance with methods of operation and use as are described below.

In use, a user typically firstly couples the delivery section 12 to the hand held drive section 16 to form the apparatus 10. The apparatus 10 is then configured to undertake a number of initialisation or validation steps including prompting of a user to select a medication type, using the external device 150 or an input such as the screen 38 of the apparatus 10, and reading a medication type data from the memory device 76 associated with the delivery section 12. These initialisation or validation steps include checking the compatibility and suitability of the delivery section 12 for the hand held drive section 16 as is further detailed below.

FIRST EXAMPLE METHOD

Configuration and Compatibility

Figure 20A:
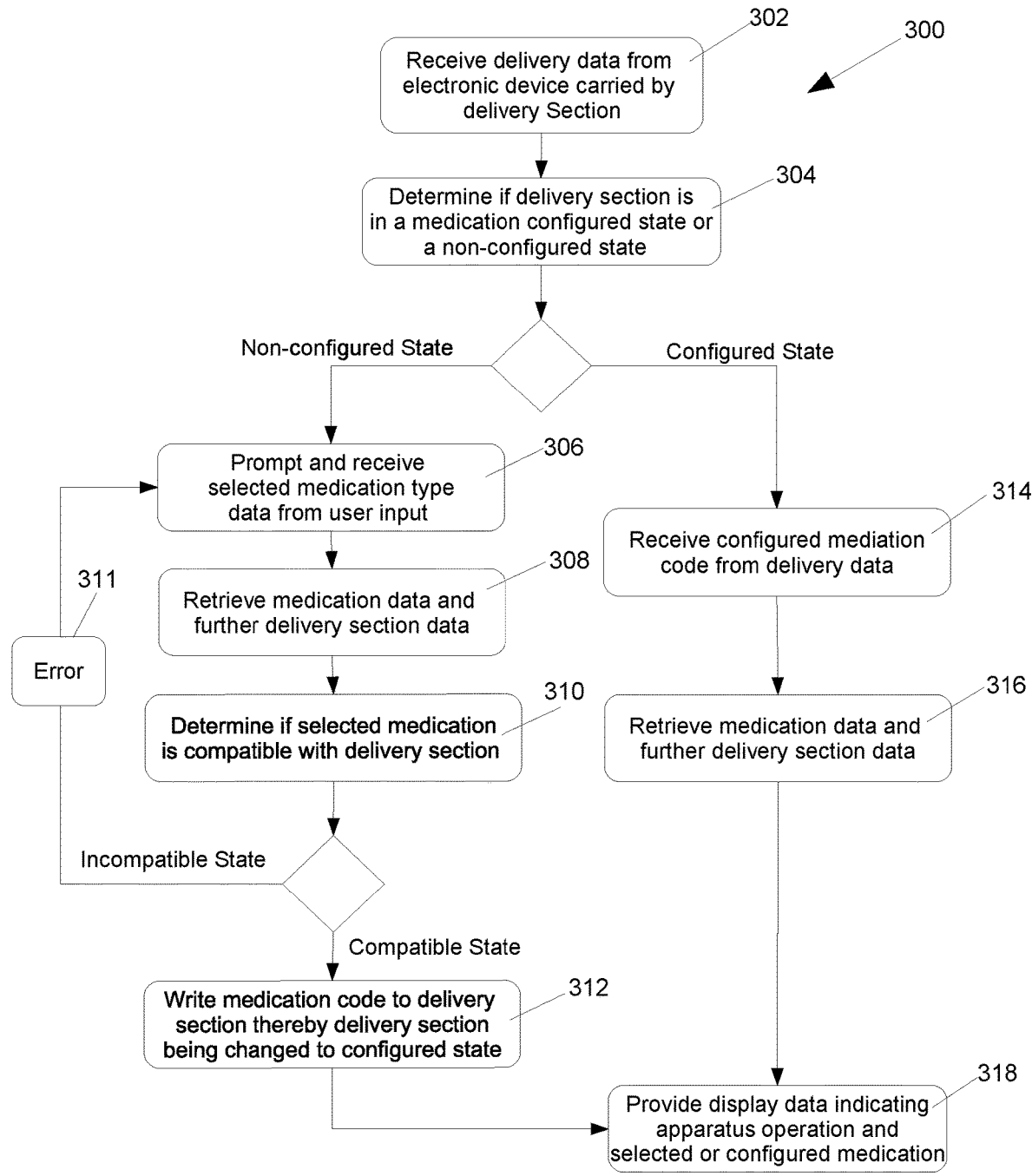
FIG. 20a is a first example of a process flow diagram illustrating a method of selecting a medication and determining the suitability of the front delivery section for use with the selected medication.

Referring to FIG. 20a there is shown a first method 300 for the initialisation and configuration of the delivery section 12 coupled to the drive section 16 to form the apparatus 10. The method is performed by the system 200 configured by software and includes, at step 302 the system 200 receiving delivery data carried by the electronic or identifier device 75, more specifically the memory device 76, of the delivery section 12. The delivery data may include identifier data to identify the particular delivery section 12, operational or configuration data associated with the particular delivery section 12, medication configuration data that may include a medication configuration identifier and if the particular delivery section 12 has already been medication configured, and may also include a medication code of a previously utilised medication used with the delivery section 12.

At step 304, the system 200 determines if the delivery section 12 is in a medication-configured state or a non-medication configured state. For example, the system 200, preferably the processor 78 of the drive section 16, is configured to determine if the delivery data includes an affirmative or negative medication configuration identifier.

In this example, the medication configuration identifier may simply be a "0" or "1" readable from the memory device 76.

At step 306, if the delivery section 12 is in a non-medication configured state, then the system 200, preferably via the external computing device 150, carries out a medication configuration routine including, at step 306 prompting and receiving a selected medication from a user to provide medication type selection data. At step 308, the system 200 then retrieves medication data (such as medication type, does rates etc) from the database 165 and retrieves further delivery data from delivery section 12 or database 165 such as delivery section type, delivery section medication type data and operational parameters of the delivery section 12.

At step 310, the system 200 determines if the selected medication type is suitable for the delivery section 12. This may include the system 200 comparing the selected medication type data to the delivery section medication type data to determine the medication compatibly and therefore determining one of a compatible state and an incompatible state. In the incompatible state, at step 311, the system 200 may provide an error message or return to prompt the user to reselect the medication type. This, in effect, at least partially disables or restricts the system 200, specifically the apparatus 10, from operation and in the incompatible state the apparatus 10 cannot be used to medicate an animal (i.e. the trigger may be disabled or the like).

At step 312, if the delivery section 12 is in the medication compatible state, then the system 200 writes a medication configuration identifier to the delivery section 12. More specifically, this may include writing to the memory device 76 to include medication data including the medication configuration identifier and a medication code or the like. The writing to the memory device 76, that preferably is EEPROM, includes locking the memory device 76 to prevent the memory device 76 from being re-written to different or new medication type. Accordingly, the medication configuration "locks" the delivery section 12 to a particular medication.

Figure 22:
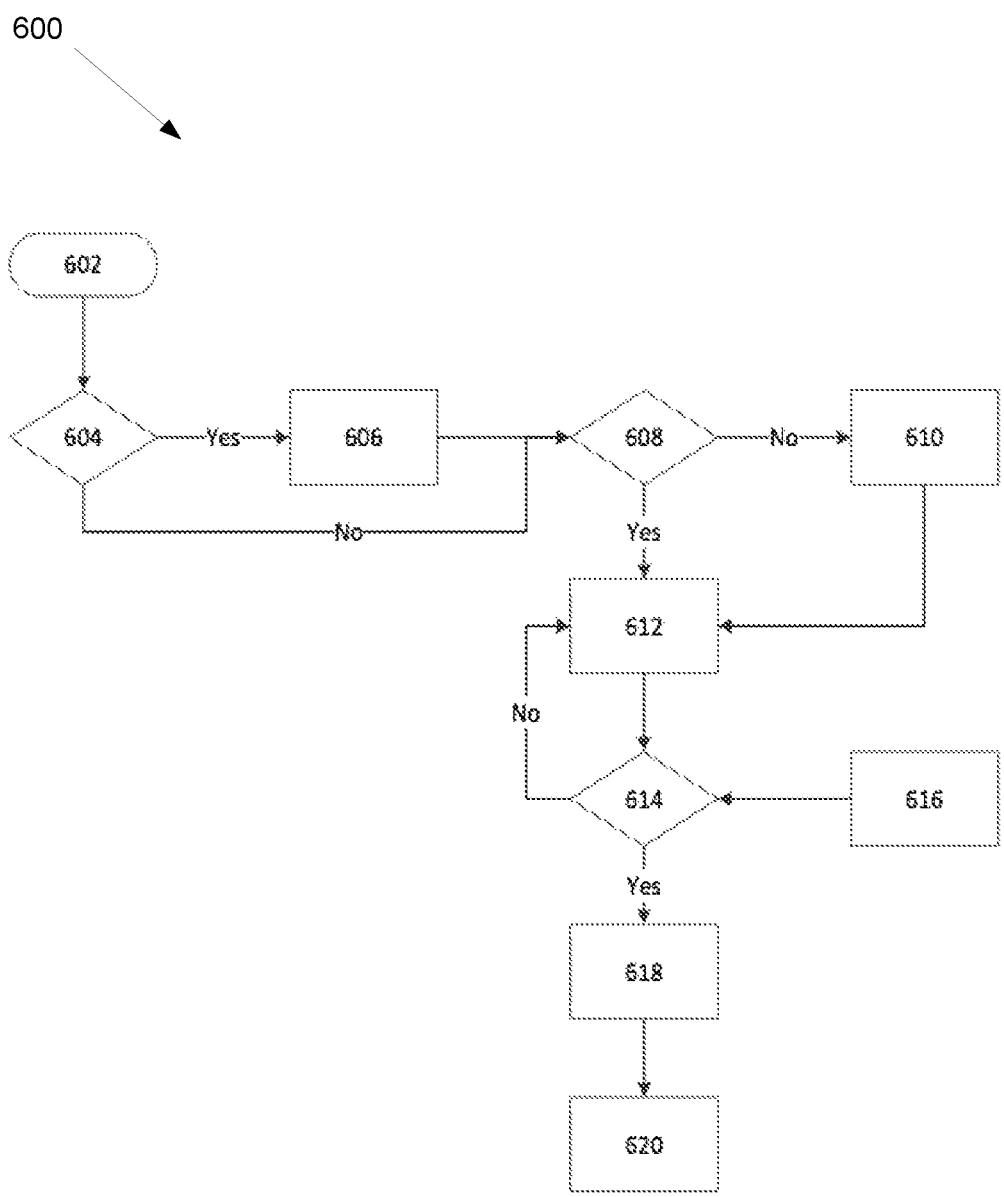
FIG. 22 is a process flow diagram illustrating a method of identifying, delivering and recording a dose of a medication substance to an animal using the first and/or second example of the apparatus.

At step 318, the system 200 is configured to display data, such as text or images via the external computing device 150 or via the display 38 of the apparatus 10, indicating the apparatus 10 is operational and configured, and the selected or configured medication type. The apparatus 10 and system 200 may then used to deliver mediation to an animal as is described below with reference to FIG. 22.

At step 314, in the configured state, the system 200 receives a configured medication code or data from the delivery data, and at step 316 the system 200 retrieves medication data and further delivery section data. Accordingly, the system 200 loads the pre-configured medication settings and is, in effect, locked to these particular medication type settings for the particular identified connected delivery section 12. The system 200 then proceeds to step 318 so as to be operational and display or indicate, in this instance, the pre-configured medication type data. The apparatus 10 and system 200 may then be used to deliver medication to an animal as is described below with reference to FIG. 22.

SECOND EXAMPLE METHOD

Configuration and Compatibility

Figure 20B:
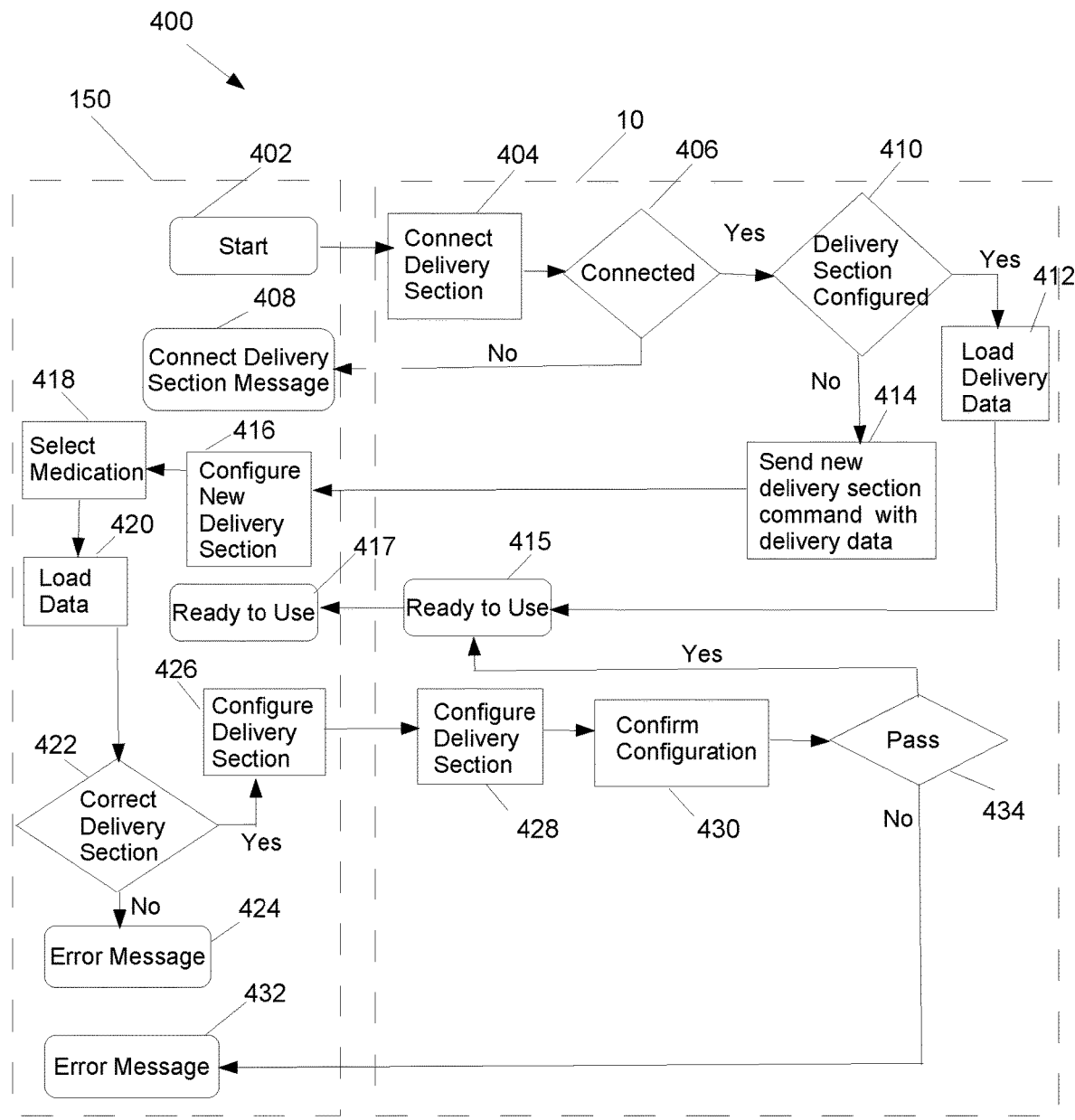
FIG. 20b is a more detailed example of the first example of a process flow diagram illustrating a method of selecting a medication and determining the suitability of the front delivery section for use with the selected medication.
Figure 21:
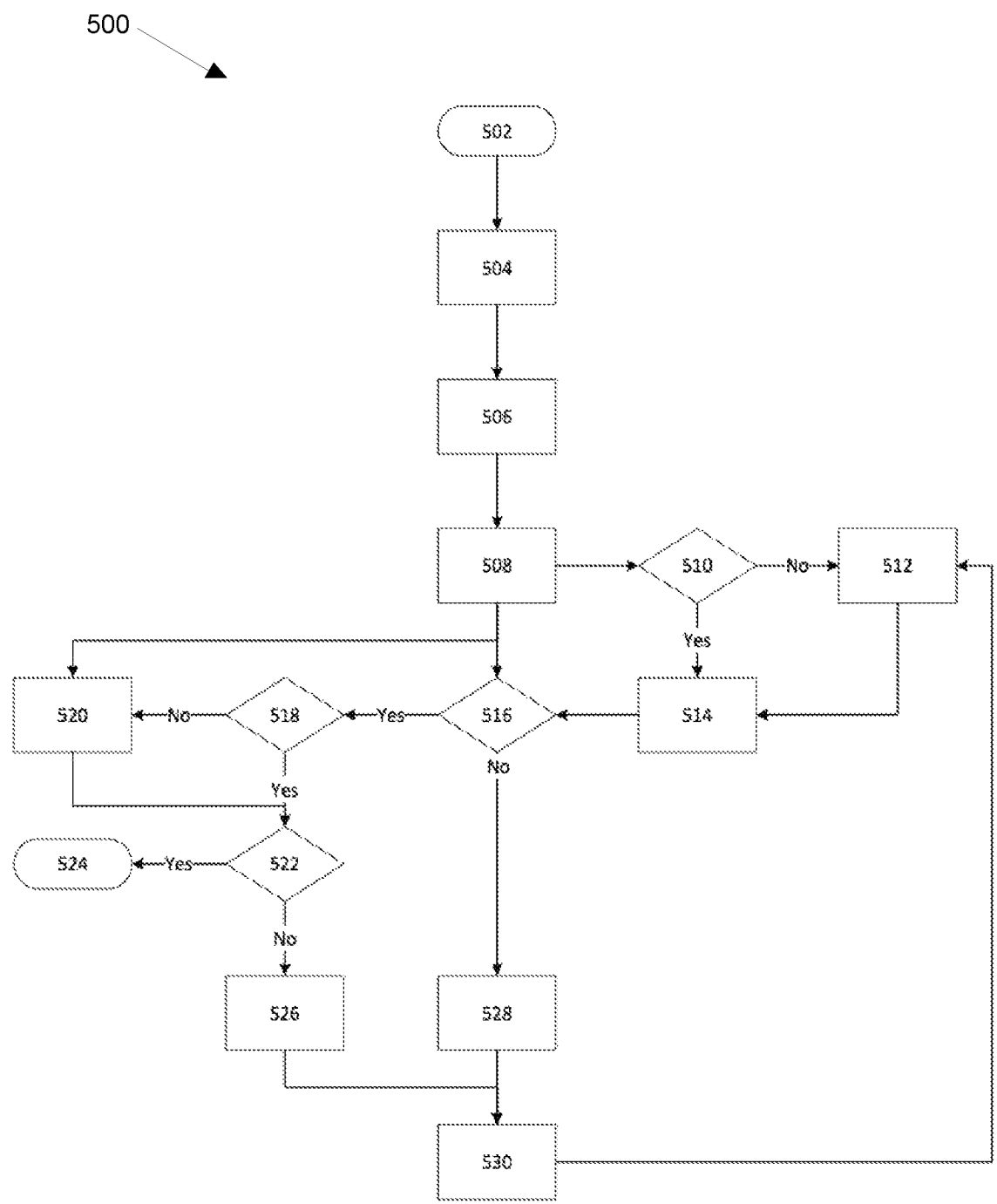
FIG. 21 is a second example of process flow diagram illustrating a method of selecting a medication and determining the suitability of the front delivery section for use with the selected medication.

Turning now to FIG. 20b, there is shown another method 400 for the configuration and compatibility determination of the delivery section 12 coupled to the drive section 16 to form the apparatus 10. This method illustrates which parts of the method are preferably, but not necessary essentially, executed by the apparatus 10 of the system 200 and the external computing device 150 of the system 200.

The method is performed by the system 200 configured by software and includes, at step 402 communicating a user interface and input device with the apparatus 10. The user interface and input device may be an associated external computing device 150, which may be a mobile device operating application software. The communication may occur via the WiFi module 80 to allow data communication between the input device 150 and the processor 78 of the apparatus 10. It is noted that in some examples, the display 38 of the apparatus 10 may be a touch screen adapted to interface with and receive user input and, in this case, the apparatus 10 carries or includes the user interface and input device. It is noted that the mobile device operating application software may, in some examples, inturn communicate with the server system 170 that may operate as an application or cloud server and the database 172 may be accessed to store and retrieve data.

At step 404, the delivery section 12 is coupled to the drive section 14 and at step 406, the control system 200 is configured to determine if the delivery section 12 is connected to the drive section 18. This may include, for example, attempting to read the memory device 76 or simply determining a positive electrical connection of the electrical connectors 54, 56.

If no delivery section 12 is connected, at step 408, the user may be prompted, such as by an indicator or message on the display 38 to connect to the delivery section 12. In this example, if the processor 78 identifies that a delivery section 12 is not connected (or may be incorrectly connected) then an error message is sent, at step 408, to the user interface and input device, which in this example, is the external computing device 150. The user may then fit or re-fit the delivery section 12.

Once the delivery section 12 is determined to be coupled or connected to the drive section 16, at step 410, the system 200 then determines if the delivery section 12 is new and in a non-configured state, or if the delivery section 12 has been previously configured and is in a medication configured state. In more detail, the processor 78 reads delivery data from the memory device 76. The delivery data includes identifier data to identify the particular delivery section 12, configuration data associated with the particular delivery section 12 and medication data which may include a medication code of a previously utilised medication used with the delivery section 12. This step is particularly important because the delivery section 12 is interchangeable and reusable, and the drive section 16, in particular, the processor 78 needs to read the delivery data in order to identify and correctly operate the delivery section 12.

If the delivery section 12 has already been used with a particular medication, being in a medication configured state, then the delivery data will typically include medication data that may include a medication code of a previously utilised medication used with the delivery section 12. The system 200, at step 412, then loads the delivery data that then configures the drive section 16 and system 200 for use with the particular attached delivery section 12. The system 200 may also send delivery data to the external computing device 150 such as sending the medication data, history data and other parameters of the particular attached delivery section 12. At steps 415 and 417, the system 200 may indicate to the user that the system 200 is ready for use. This may be displayed or indicated at the apparatus 10 and/or at the external computing device 150.

If the delivery section 12 is not configured to a particular medication, being in a non-medication configured state, the system 200 then undertakes a medication configuration routine including, at step 414 communicating delivery data including delivery section configuration data to the external computing device 150, and at step 416 the external computing device 150 initiates a local routine to guide the user through configuring the particular delivery section 12 to a particular medication.

At step 418, the user selects a medication type using the input device provided by the external computing device 150. The medication type may be entered as a code or the user may select the medication type from a predefined list.

At step 420, selected medication or substance type data is loaded by the system 200 via the computing device 150 either from local memory or from an external database accessible 172 via the server system 170. The selected medication type data includes a code for the medication type and medication values and information such as dose rates (mm/kG).

At step 422, the system 200 then undertakes a compatibility check to determine if the correct type of delivery section 12 is connected for the selected medication. For example, the delivery data may include delivery section type data indicating if the delivery section 12 is suitable for one of injecting, drenching or back lining, and delivery medication type data that may include data indicating the types of medication that are suitable for the particular delivery section. The delivery section type data and/or delivery medication type data may also be loaded from an external database 160 or 172 once the delivery section 12 is identified by the system 200.

The system 200 then conducts comparative operations, via the computer device 150, to determine if the delivery type medication data and selected medication type data are compatible and/or if the delivery section type and the selected medication type data both indicate the same or a compatible delivery section type being, for example, one of injecting, drenching or back lining. If the type of delivery section 12 is not compatible with the selected medication, then the method moves to step 424 in which indications are provided to the user, for example via the display or computer device 150, that the incorrect delivery part 12 is fitted. The system 200 is also configured enter at least partially inoperative state in which the apparatus 10 is unable to deliver medication.

At step 426, the system 200 configures the delivery section 12 to the particular selected medication. This includes the computer device 150 of the system 200 communicating new delivery data including medication type data to the particular delivery section 12. At step 428, the system 200, via the processor 78, is then configured to write specific configuration and medication data to the memory device 76 carried by the particular delivery section 12 and locks the specific configuration data to the memory device 76 which is preferably EEProm memory. The specific configuration data includes the selected medication type data or data to represents the selected medication type data so that when the memory device 76 is again read at a later stage the processor 78 is able to determine the medication history of the particular delivery section 12. Accordingly, once a particular delivery section 12 is utilised with a particular selected medication, the particular delivery section 12 is, in essence, hard coded to always be only usable with the particular selected medication. This assists with inhibiting medication cross-contamination.

At step 430, the processor 78 then undertakes a further medication compatibility check to determine if the connected delivery section 12 is suitable for the selected medication type. During this routine the processor 78 receives delivery data from the now locked memory device 76, in particular data representing or used to determine, delivery medication type data which indicates the particular medication type associated with the connected delivery section 12. The processor 78 also receives, the selected medication type data representing the selected medication type selected for use. The processor 78 then conducts processing operations to determine compatibility of the delivery medication type and the selected medication type to provide compatibility data representing at least one of a compatible medication state and an incompatible medication state.

At step 434, if the compatibility data indicates the compatible medication state, the processor 78 enables the apparatus 10 to a ready to medicate condition, at step 415, in which the user may operate the apparatus 10 in accordance with the method 600 for delivering a substance to an animal as is further described below. The processor 78 may be configured to send a ready signal to the display 38 or to the indicator lights 40. However, if the compatibility data indicates the incompatible medication state, the system 200 is configured to at least partially disable operation of the medication delivery apparatus 10 so as to inhibit delivery of medication. At step 434, the processor 78 may be configured to send an error signal to the computing device 150, to the display 38 or to the indicator lights 40. In the incompatible or error medication state, the particular delivery section 12 may need to be removed and interchanged at step 432.

THIRD EXAMPLE METHOD

Configuration and Compatibility

Figure 10:
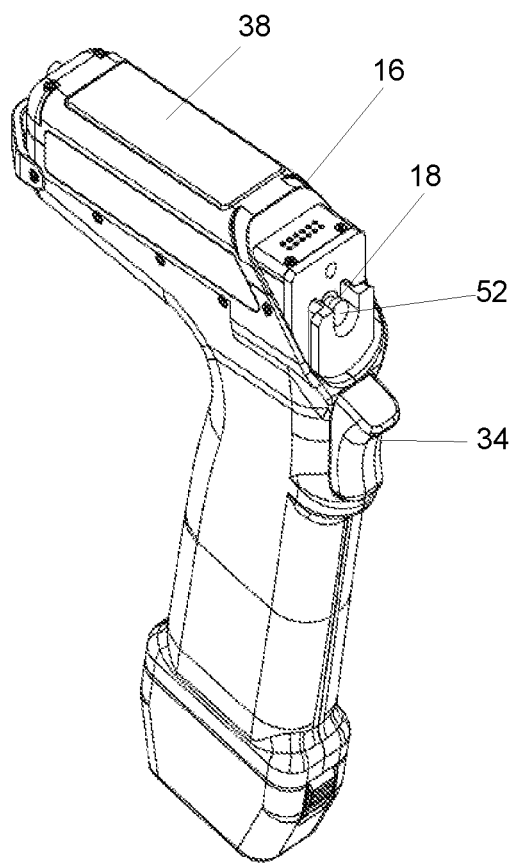
FIG. 10 is a front perspective view illustrating the rear drive section with the front delivery section in the de-coupled condition.
Figure 11:
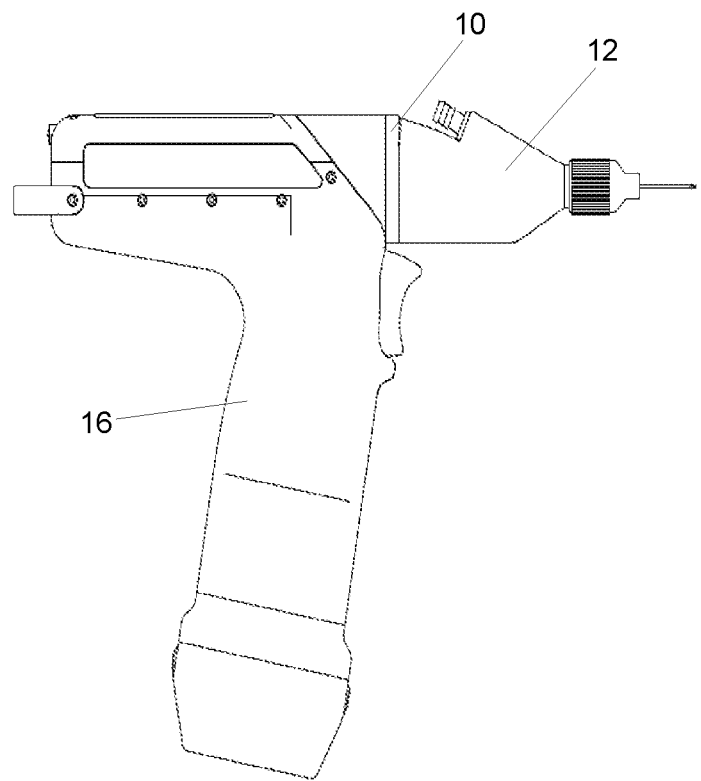
FIG. 11 is a side view illustrating the hand held apparatus including the front delivery section and the rear hand held drive section in the coupled condition.
Figure 12:
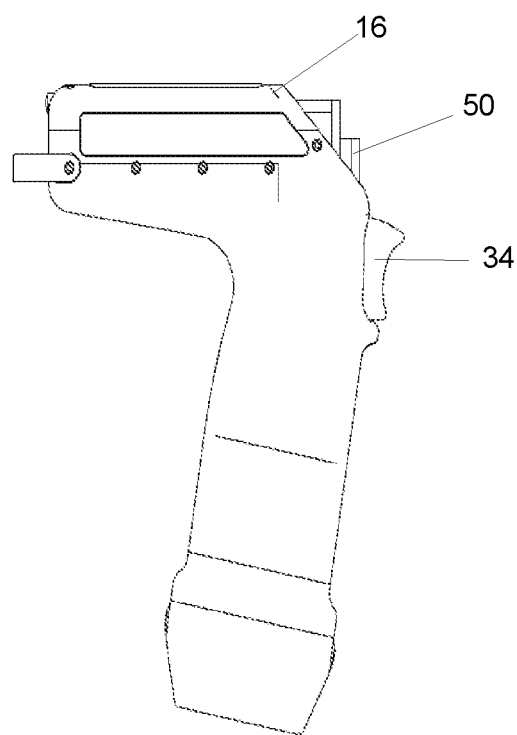
FIG. 12 is a side view illustrating the rear drive section with the front delivery section in the de-coupled condition.

In more detail, referring to FIG. 10, there is shown yet another example a method 500 for the confirmation and compatibility determination of the delivery section 12 coupled to the drive section 16 to form the apparatus 10. The method including, at step 502 an input device such as an external computing device 150, which may be a mobile device, being launched and communicated with the apparatus 10 at step 504. The communication may occur via the WiFi module 80 to allow data communication between the input device 150 and the processor 78 of the apparatus 10. It is noted that in some examples, the display 38 may be a touch screen and, in this case, the apparatus 10 carries the input device.

At step 506, a user selects a medication type using the input device. The medication type may be entered as a code or the user may select the medication type from a predefined list.

At step 508, a medication specification type data is loaded by the processor 78 either from local memory carried by the apparatus 10 or from an external source such as an external mobile device or an external database accessible via a webserver. The selected medication type data includes a code for the medication type and information such as dose rates (mm/kG).

At step 510, the processor 78 is configured, by software, to determine if the delivery section 12 is connected to the drive section 18. This may include, for example, attempting to read the memory device 76 or simply determining a positive electrical connection of the electrical connectors 54, 56. If no delivery section 12 is connected, at step 312, the use may be prompted, such as by an indicator or message on the display 38 to connect to the delivery section 12.

At step 514, if the delivery section 12 is coupled to the drive section 16, and the processor 78 is configured to read delivery data from the memory device 76. The delivery data includes identifier data to identify the particular delivery section 12, configuration data associated with the particular delivery section 12 and medication data which may include a medication code of a previously utilised medication used with the delivery section 12. This step is particularly important because the delivery section 12 is interchangeable and the driver section 16, in particular, the processor 78 needs to read the delivery data in order to identify and correctly operate the delivery section 12.

The configuration data may include variables such as volume of the delivery cylinder 81, volumetric rates such as mL of substance discharged for mm of linear movement of the substance plunger 80. Other variables may include the total stroke length. The identifier data may include data to indicate the type of delivery section 12 which may be for example delivery sections 12 for injecting, drenching or back-lining.

At step 516, the processor 78 then undertakes an initial compatibility check to determine if the correct type of delivery section 12 is connected for the selected medication. For example, the delivery data may include data that the delivery section 12 is suitable for one of injecting, drenching or back lining and selected medication type data may include data indicating the medication is suitable for one of injecting, drenching or back lining. The processor 78 then conducts comparative operations to determine if the delivery data and the selective medication type data both indicated the same delivery type being one of injecting, drenching or back lining. If the type of delivery section 12 is not compatible with the selected medication, then the method moves to steps 528 and 530 in which indications are provided to the user, for example via the display, that the incorrect delivery part 12 is fitted. The processor 78 is also configured an at least partially inoperative state in which the apparatus 10 is unable to deliver medication.

At step 518, the processor 78 then undertakes a further identification step in which the processor 78 determined if the delivery section 12 has been previously utilised and configured. In this step, the processor 78 retrieves or processes retrieved delivery data including the identification data from the memory device 76 carried by the particular delivery section 12. The identification data may include prior use data which indicates if the particular delivery section 12 has been previously configured or used.

At step 520, if the prior use data indicates that the particular delivery section 12 has not been previously used or configured, the processor 78 then writes specific configuration data to the memory device 76 carried by the particular delivery section 12 and locks the specific configuration data on to the memory device 76 which is preferably EEProm memory. The specific configuration data includes the selected medication type data or data to represents the selected medication type data so that when the memory device 76 is again read at a later stage the processor 78 is able to determine the medication history of the particular delivery section 12. Accordingly, once a particular delivery section 12 is utilised with a particular selected medication, the particular delivery section 12 is, in essence, hard coded to always be only usable with the particular selected medication. This assist with inhibiting medication cross-contamination.

At step 522, the processor 78 then undertakes a secondary medication compatibility check to determine if the connected delivery section 12 is suitable for the selected medication type. During this routine the processor 78 receives delivery data from the now locked memory device 76, in particular data representing or used to determine, delivery medication type data which indicates the particular medication type associated with the connected delivery section 12. The processor 78 also receives, the selected medication type data representing the selected medication type selected for use. The processor 78 then conducts processing operations to determine compatibility of the delivery medication type and the selected medication type to provide compatibility data representing at least one of a compatible medication state and an incompatible medication state.

At step 524, if the compatibility data indicates the compatible medication state, the processor 78 enables the apparatus 10 to a ready to medicate condition in which the user may operate the apparatus 10 in accordance with the method 600 for delivering a substance to an animal as is further described below. The processor 78 may be configured to send a ready signal to the display 38 or to the indicator lights 40.

At step 526, if the compatibility data indicates the incompatible medication state, the processing system 78 is configured to at least partially disable operation of the medication delivery apparatus 10 so as to inhibit delivery of medication. At step 526, the processor 78 may be configured to send an error signal to the display 38 or to the indicator lights 40. In the incompatible medication state, the particular delivery section 12 may need to be removed and interchanged at step 530. The routine then proceeds to step 512 where a new delivery section 12 is connected to the drive section 12.

FOURTH EXAMPLE METHOD

Delivering a Substance to an Animal

Referring now to FIG. 10, a method 600 for delivering a substance to an animal and the associated operation of the apparatus 10 is further described. In the method below, it is assumed the delivery section 12 is connected to the drive section 16 and is in the operative compatible medication state as described above with reference to methods 300 and 400.

At step 602, a particular animal is selected for medication and at step 604, if the animal includes a identification means such as an animal RFID tag, an animal identification step is undertaken at step 606 in which the animal RFID tag is scanned or read by the RFID reader 70 of the apparatus 10. The RFID reader may be activated by user actuation of the trigger and the animal identification data may be received by and processed by the processor 78.

At step 608, the system 200 is configured to determine if a fixed dose or a calculated dose is to be administered. If the animal does not include an identification means or if the animal is not identifiable the system 200, preferably the processor 78, determines that a fixed or pre-determined dose should be applied to the animal. This pre-determined dose or dose rate may be included in the selected medication type data as was described above in relation to methods 300 or 400. The fixed dose may be inputted by a user or predetermined by the system 200.

However, if the animal information is available, the control system 200 then initiates an animal identification lookup step, at step 610, wherein the identification of the animal is matched to a pre-defined database or stored animal information located in the memory of the control system 200 or an externally accessible device or database such as database 160. This stored information may be pre-loaded or stored in the memory and may include animal parameters such as weight, height, age, sex and/or other similar information.

On matching the animal identification with the stored information the control system 200 retrieves the animal parameters at an animal parameters lookup step. The animal parameters may include the animal weight, type and age as well as related information which is used to calculate the dose rate. In some examples, the dose may be manually inputted by the user or may be a fixed dose. However, in this example, the dose rate is calculated at a dose rate calculation or processing step using animal parameters and medication parameters. The medication parameters may include information such as type of medication and dose rate lookup tables, for example dose in ml/kg for selected medications, which are utilised in the dose rate calculation. The medication parameters may be pre-loaded or stored in the memory and accessed by the processor.

The dose rate calculation includes determining how far to linearly move to shaft 104 and hence the plunger 80 to deliver the dose, or pre-determined quantity, of the medication to the animal. The system 200 receives delivery section data that includes volume parameters such as mL/mm. So, for example, if the determined dose is 5 mL, and the volume parameter, V, of the delivery section 12 is, 1 mL/mm, the system 200 is configured to determine a linear movement parameter, L, that in this case would 5 mm (i.e 5 mm linear plunger movement is required to expel 5 mL to substance to the animal). The linear position sensor 106 continuously monitors or measures this linear distance to provide position feedback for the control system 200.

At step 612, the trigger 34 is actuated to activate the apparatus 10, via the control system 200, to begin delivery of the medication through the application delivery part or tip 22. Turning now to the flow and delivery of the fluid substance in more detail, by way of example only, the process for medication flow into and out of the apparatus 10 may function as follows.

Beginning with the medication reservoir 77 in the expanded state with the delivery plunger 80 located toward the rear end of the delivery cylinder 81. It is assumed here that the apparatus 10 has undergone an initial priming step whereby air is evacuated from the medication reservoir 77 and the medication reservoir 77 is filled with the substance.

In the first example of the apparatus 10, when trigger 34 is activated or pulled the pneumatic control valve 114 is moved to a fill position allowing a pressurised gas, for example, gas from the pressure canister 31, into the drive cylinder 100 to pressurise and urge plunger 98 forward from a first position toward a second position which, in the coupled condition, in turn moves the delivery plunger 80 and hence the medication reservoir 77 toward the contracted state. The fluid pressure inside the medication reservoir 77 thereby opening the valve 94 and maintaining the valve 92 in the ordinarily closed position. It is noted that in the second example of the apparatus 10, the drive arrangement 18 is electrically powered and the electric drive arrangement 900 including the electric motor 902 is activated by the control system 200 to move the plunger 80 in the same manner as described above.

At step 616, during this movement, the measurement or linear position sensor 106 is measuring the distance moved by the rod 104 and hence movement of the delivery plunger 80 coupled thereto. The distance measurement is converted by the control system 200, to a volume of substance administered or a dose. The measurement data provided to the processor 78 allows for feedback control of the delivery plunger 80 and medication delivery therefrom.

At step 614, once the control system 200 determines a pre-determined dose, either the fixed dose or the calculated dose, has been reached, the exhaust pneumatic control valve 116 is moved to an open or re-fill position in which an evacuation or exhaust port is opened between the drive cylinder 100 and the external environment. This allows the return spring 103 to move the drive plunger 98 back to the first position in which the medication reservoir 77 is again in the expanded state. During this movement, the medication inlet valve 92 moves to an open position which allows the flow of the substance into the medication reservoir 77 via the conduit 88. The valve 94 moves to a closed position to prevent air entering the medication reservoir 77 and maintains the vacuum. The drive plunger 80 then reaches its mechanical limits and is retained in the first position until the trigger 34 is next actuated. The couplings 50, 52 between the drive plunger 98 and delivery plunger 80 result in the delivery plunger 80 being actuated in a likewise motion and being controlled by the movement of the drive plunger 98.

Again, it is noted that in the second example of the apparatus 10, the drive arrangement 18 is electrically powered and the electric drive arrangement 900 including the electric motor 902 is activated by the control system 200 to move the plunger 98 in the same manner as described above. In the second example, the micro-chain 908 moves the shaft 104 and hence the drive plunger 80 in both the forward and reverse directions and therefore a return spring 103 is not required in the second example.

At step 618, dose data representing the measured delivered dose is written internal memory 84 carried by the drive section 12, and at step 620 the dose data is written to memory of the external computing device 150, such as a mobile device. The apparatus 10 then enters a ready or stand-by mode awaiting the next actuation of the trigger 34. Preferably, the dose data is also written to the server system 170 and the database 172 thereby enabling synchronising of the dose data between the apparatus 10, external computing device 150 and server system 170. The recorded dose data may include or be associated with the following animal identification data, mediation type data, dose amount, batch number, user ID, farm ID, date, time, apparatus serial number including delivery section serial number and application software version.

Advantageously, there has been described an apparatus having a split arrangement with a removable and interchangeable delivery section and a main drive section which operates and controls the delivery section. The delivery section may be considered an adaptor or interchangeable head which includes a medication reservoir and plunger which when coupled to the main drive section is actuated and controlled by the main drive section. The delivery section having the medication reservoir fully separates any medication carried by or associated with the delivery section from the main drive section. The interchangeable delivery section also allows different types of the delivery section to be coupled with a common main drive section providing the apparatus with a high level of flexibility.

Further advantageously, the delivery section carries an identifier or memory device that uniquely identifies the delivery section such as providing a code or other data to identify the delivery section to the control system. This identifier allows the delivery section to be associated with a particular medication type, such as a previously used medication, and may be associated with operational parameters of the delivery section to enable the main drive section to correctly operate the delivery section. The memory device may also be preferably hard coded on the first use of the delivery section with a particular medication type such that delivery section is, in-effect, locked to be only used with that particular medication type.

Accordingly, the apparatus in conjunction with the control system is able to determine if the delivery section has been previously used and configured to a particular type of medication, and if in a configured state, restrict the delivery section to being used with the particular configured medication. However, if the delivery section is new and in a non-configured state, the system able to receive a user selected medication, check that the connected delivery section is compatible with the user selected medication, and then configure the delivery section for use with the user selected medication. The system then is able to "lock" the memory device to the configured medication and thereby the delivery section being in the configured state.

Furthermore, the memory device of the delivery section may include the operational parameters and these may be stored to the memory device for reading by the processor carried by the delivery section to enable the main drive section to correctly operate the delivery section. Accordingly, when the main drive section is configured to deliver a particular medication type, the control system is able to check that the attached delivery section is medication compliant or compatible, and also have access to operational parameters for operation of the delivery section. This provides highly advantageous medication compliance functionality.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any known matter or any prior publication is not, and should not be taken to be, an acknowledgment or admission or suggestion that the known matter or prior art publication forms part of the common general knowledge in the field to which this specification relates.

While specific examples of the invention have been described, it will be understood that the invention extends to alternative combinations of the features disclosed or evident from the disclosure provided herein.

Many and various modifications will be apparent to those skilled in the art without departing from the scope of the invention disclosed or evident from the disclosure provided herein.

The claims defining the invention are as follows:

1. A hand held apparatus for delivering a substance to an animal, the apparatus comprising:
   a hand held frame comprising a drive section including a drive arrangement, the drive arrangement having an adjustable stroke, the hand held frame further comprising a trigger;
   a removable delivery section including a delivery arrangement configured to deliver the substance to the animal through a delivery part;
   a substance reservoir in fluid communication with the removable delivery section;
   a control system;
   the removable delivery section:
      being removably mechanically coupled to the hand held frame such that the drive arrangement of the hand held frame is configured to actuate the delivery arrangement of the removable delivery section when mechanically coupled;
      being removably electrically coupled to the hand held frame and having an electronic device configured to communicate with the controller;
      having a first one-way valve configured to allow the substance to flow from the substance reservoir into a main delivery conduit and a second one-way valve located at a distal end and configured to allow the substance to flow from the main delivery conduit to the delivery part;
   the control system being configured to calculate a stroke length for the drive arrangement and receive input from the trigger, and in response to the input, cause the drive arrangement to operate the removable delivery section at the stroke length;
   wherein the electronic device is configurable to receive and configuration information and substance type information transmitted from the control system, and further having an indicator indicating either a substance configured state and a substance non-configured state.

2. The hand held apparatus of claim 1, the control system comprising a processor mounted in the hand held frame.

3. The hand held apparatus of claim 1, the control system comprising a processor mounted in an external computing device.

4. The hand held apparatus of claim 1, the control system being configured to receive an electronic identifier from the electronic device of the removable delivery system and change the substance type information on the electronic identifier with a substance type.

5. The hand held apparatus of claim 1, the control system being further configured to:
   determine that an electronic identifier is in the substance a non-configured state;
   determine a substance type; and
   change the substance type information on the electronic identifier to the substance type.

6. The hand held apparatus of claim 1, said trigger creating an electrical input to said control system, said electrical input causing said drive section to actuate.

7. The hand held apparatus of claim 6, said trigger comprising a finger-operated trigger button.

8. The hand held apparatus of claim 1, said delivery part comprising a drenching tube.

9. The hand held apparatus of claim 1, said removable delivery section being coupled to said hand held frame using a locking mechanism.

10. The hand held apparatus of claim 9, said locking mechanism comprising a snap fit.

11. The hand held apparatus of claim 1, the drive section being oriented substantially parallel to the delivery arrangement when the removable delivery section is attached, and a gun-shaped handle section being oriented off axis from the drive section.

12. A system for delivering a dose of a substance to an animal, the system comprising:
   an interchangeable delivery section including a delivery arrangement adapted to deliver the substance to the animal and an electronic device, said interchangeable delivery section comprising:
      a connection to a substance reservoir containing a substance;

a first one-way valve configured to allow the substance to flow from the substance reservoir into a main delivery conduit; and a second one-way valve configured to allow the substance to flow from the main delivery conduit to a delivery part, the second one-way valve being located at a distal end of the interchangeable delivery section;

a hand held frame comprising a drive section including a drive arrangement configured to actuate the delivery arrangement in a coupled condition in which the interchangeable delivery section is mechanically coupled to the drive section;

the hand held frame further comprising a gun shaped handle section configured to be held in a hand of an operator, the hand held frame further comprising a trigger, the trigger being configured to be actuated by a finger of the hand of the operator; and a control system configured to communicate with the electronic device of the interchangeable deliver section and selectively operate the drive arrangement in the coupled condition;

wherein the electronic device is configured to receive and store delivery information and the control system is configured to transmit the delivery information to the electronic device and further to receive and process the delivery information;

wherein the delivery information comprises a measured delivery dose;

wherein the delivery information comprises data indicating that the delivery section is in one of a substance configured state and a substance non-configured state, and wherein the control system is configured to read the data and determine that the delivery section is in one of the substance configured state and the substance non-configured state;

wherein the control system is further configured to change the electronic device on the removable delivery section to a substance configured state and further configured to change the delivery information to add a substance type corresponding to the substance in the substance reservoir.

13. The system of claim 12, wherein, in the substance non-configured state, the system is configured to receive selected substance type data and determine that the selected substance type data and the delivery section are in one of a medication compatible state and a medication incompatible state.

14. The system of claim 13, wherein, in the medication compatible state, the control system is configured to write substance type data indicative of the selected substance to the electronic device carried by the delivery section thereby configuring the delivery section to the substance configured state.

15. The system of claim 12, wherein the control system is configured to receive substance type selection data and wherein the delivery information includes delivery substance type data associated with the interchangeable delivery section, wherein the control system is configured to determine that the substance type selection data and delivery substance type data represent compatible substances, and restrict operation of the system when the substances are incompatible.

16. The system of claim 12, wherein the control system is configured to receive substance type selection data and wherein the delivery information includes delivery section type data indicating the type of coupled interchangeable delivery section, wherein the control system is configured to determine that the substance type selection data and delivery section type data represent a compatible combination, and restrict operation of the system when the combination of substance type selection data and delivery section type data is not compatible.

17. The system of claim 12, said hand held frame comprising a trigger, said trigger creating an electrical input to said control system, said electrical input causing said drive section to actuate.

18. The hand held apparatus of claim 17, said trigger comprising a finger-operated trigger button.

* * * * *